(12) United States Patent
Shin et al.

(10) Patent No.: US 12,391,960 B2
(45) Date of Patent: Aug. 19, 2025

(54) METHODS AND CONSTRUCTS FOR PRODUCTION OF LENTIVIRAL VECTOR

(71) Applicant: LONZA WALKERSVILLE, INC., Walkersville, MD (US)

(72) Inventors: Young Shin, Pearland, TX (US); Anandita Seth, Pearland, TX (US); Bingnan Gu, Pearland, TX (US)

(73) Assignee: LONZA WALKERSVILLE, INC., Walkersville, MD (US)

( * ) Notice: Subject to any disclaimer, the term of this patent is extended or adjusted under 35 U.S.C. 154(b) by 0 days.

(21) Appl. No.: 18/680,137

(22) Filed: May 31, 2024

(65) Prior Publication Data
US 2024/0336936 A1 Oct. 10, 2024

Related U.S. Application Data

(62) Division of application No. 17/001,114, filed on Aug. 24, 2020, now Pat. No. 12,037,599.

(60) Provisional application No. 62/890,904, filed on Aug. 23, 2019.

(51) Int. Cl.
| | | |
|---|---|---|
| C12N 15/867 | (2006.01) | |
| C07K 14/16 | (2006.01) | |
| C12N 5/071 | (2010.01) | |
| C12N 9/12 | (2006.01) | |
| C12N 15/86 | (2006.01) | |

(52) U.S. Cl.
CPC .......... *C12N 15/867* (2013.01); *C07K 14/161* (2013.01); *C07K 14/162* (2013.01); *C07K 14/163* (2013.01); *C12N 5/0686* (2013.01); *C12N 9/1241* (2013.01); *C12N 15/8673* (2013.01); *C12N 15/8676* (2013.01); *C12N 15/86* (2013.01); *C12N 2740/15051* (2013.01); *C12N 2740/16052* (2013.01); *C12N 2760/20222* (2013.01)

(58) Field of Classification Search
CPC .. C07K 14/161; C07K 14/163; C12N 15/867; C12N 2740/15051; C12N 2740/16052
See application file for complete search history.

(56) References Cited

U.S. PATENT DOCUMENTS

| | | | |
|---|---|---|---|
| 7,262,049 B2 | 8/2007 | Marasco | |
| 7,745,179 B2 | 6/2010 | Mcarthur et al. | |
| 9,169,491 B2 | 10/2015 | Truran et al. | |
| 9,441,245 B2 | 9/2016 | Chiara et al. | |
| 10,087,463 B2 | 10/2018 | Fraser et al. | |
| 10,125,352 B2 | 11/2018 | Fenard | |
| 10,465,169 B2 | 11/2019 | Boudeffa et al. | |
| 10,699,284 B2 | 6/2020 | Sheth et al. | |
| 2009/0042297 A1 | 2/2009 | George | |
| 2016/0267432 A1 | 9/2016 | Hodges | |
| 2016/0350715 A1 | 12/2016 | Minvielle | |
| 2017/0051309 A1 | 2/2017 | Lesch et al. | |
| 2017/0368201 A1 | 12/2017 | Gu et al. | |
| 2018/0320147 A1 | 11/2018 | Johnson et al. | |
| 2019/0055568 A1 | 2/2019 | Pule et al. | |
| 2019/0093126 A1 | 3/2019 | High et al. | |
| 2019/0180289 A1 | 6/2019 | Klavins | |
| 2019/0211360 A1 | 7/2019 | Marceau et al. | |
| 2020/0123505 A1 | 4/2020 | Johnson et al. | |
| 2020/0157567 A1 | 5/2020 | Cawood et al. | |
| 2020/0208121 A1 | 7/2020 | Hewitt et al. | |
| 2020/0277629 A1 | 9/2020 | Cawood et al. | |

FOREIGN PATENT DOCUMENTS

| | | |
|---|---|---|
| EP | 3456822 A1 | 3/2019 |
| WO | 2011/097447 A3 | 8/2011 |
| WO | 2017/089308 A1 | 6/2017 |
| WO | 2017/144892 A1 | 8/2017 |
| WO | 2017/144893 A1 | 8/2017 |

OTHER PUBLICATIONS

Gil, Alberto Molina. (2017) Lentiviral vector packaging cell line development using genome editing to target optimal loci discovered by high-throughput DNA barcoding [Doctoral Thesis, Institution University College London].
Heinz et al., "Retroviral and Transposon-Based Tet-Regulated All-In-One Vector with Reduced Background Expression and Improved Dynamic Range," Human Gene Therapy 22: 166-176 (2011).
Cary et al., "Transposon mutagenesis of baculoviruses: Analysis of *Trichoplusia ni* transposon IFP2 insertions within the FP-locus of nuclear polyhedrosis viruses," Virology 172(1): 156-169 (1989).
Chu et al., "SV40 DNA transfection of cells in suspension: analysis of the efficiency of transcription and translation of T-antigen," Gene 13(2): 197-202 (1981).
Elick et al., "Excision of the piggyBac transposable element in vitro is a precise event that is enhanced by the expression of its encoded transposase," Genetica 98(1): 33-41 (1996).
Elick et al., "PCR analysis of insertion site specificity, transcription, and structural uniformity of the Lepidopteran transposable element IFP2 in the TN-368 cell genome," Genetica 97(2): 127-139 (1996).
Fraser et al., "Acquisition of Host Cell DNA Sequences by Baculoviruses: Relationship Between Host DNA Insertions and FP Mutants of *Autographa californica* and *Galleria mellonella* Nuclear Polyhedrosis Viruses," Journal of Virology 47(2): 287-300 (1983).
Fraser et al., "Assay for Movement of Lepidopteran Transposon IFP2 in Insect Cells Using a Baculovirus Genome as a Target DNA," Virology 211(2): 397-407 (1995).

(Continued)

*Primary Examiner* — Jeffrey S Parkin
(74) *Attorney, Agent, or Firm* — MEDLER FERRO WOODHOUSE & MILLS PLLC

(57) ABSTRACT

The present disclosure relates to methods for producing lentiviral vector-producing cells. Specifically the methods utilize two plasmids, rather than four, to provide the required packaging elements and transfer vector to a cell, allowing for the production of a large number of lentiviral producer cells, including suspension-based cells, and the production of high amounts of lentivirus. These methods allow for the production of cells that can be later induced to produce lentivirus, and can be tailored to include a specific gene of interest.

13 Claims, 10 Drawing Sheets

(56) References Cited

OTHER PUBLICATIONS

Fraser et al., "Precise excision of TTAA-specific lepidopteran transposons *piggyBAC* (IFP2) and *tagalong* (TFP3) from the baculovirus genome in cell lines from two species of *Lepidoptera*," Insect Molecular Biology 5(2): 141-151 (1996).
Graham et al., "A new technique for the assay of infectivity of human adenovirus 5 DNA," Virology 52(2): 456-467 (1973).
Handler et al., "The lepidopteran transposon vector, *piggyBAC*, mediates germ-line transformation in the Mediterranean fruit fly," Proc. Natl. Acad. Sci. USA 95(13): 7520-7525 (1998).
Hellmund et al., "Coordination of Genomic RNA Packaging with Viral Assembly in HIV-1," Viruses 8(192): 1-13 (2016).
Lobo et al., "Transposition of the *piggyBAC* element in embryos of *Drosophila melanogaster, Aedes aegypti* and *Trichoplusia ni*," Molecular and General Genetics 261(4-5): 803-810 (1999).
Merten et al., "Production of lentiviral vectors," Molecular Therapy—Methods & Clinical Development 3:16017 (2016).
Mullick et al., "The cumate gene-switch: a system for regulated expression in mammalian cells," BMC Biotechnology 6(43): 1-18 (2006).
Wang et al., "TTAA serves as the target site for TFP3 lepidopteran transposon insertions in both nuclear polyhedrosis virus and *Trichoplusia ni* genomes," Insect Molecular Biology 1(3): 109-116 (1993).
Yao et al., "Tetracycline Repressor, tetR, rather than the tetR-Mammalian Cell Transcription Factor Fusion Derivatives, Regulates Inducible Gene Expression in Mammalian Cells," Human Gene Therapy 9(13): 1939-1950 (1998).

METHODS AND CONSTRUCTS FOR PRODUCTION OF LENTIVIRAL VECTOR

CROSS-REFERENCE TO RELATED APPLICATIONS

The present application claims benefit of U.S. Provisional Patent Application No. 62/890,904, filed Aug. 23, 2019, the disclosure of which is incorporated by reference herein in its entirety.

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

FIELD OF THE INVENTION

The present disclosure relates to methods for producing lentiviral vector-producing cells. Specifically the methods utilize two plasmids, rather than four, to provide the required packaging elements and transfer vector to a cell, allowing for the production of a large number of lentiviral producer cells, including suspension-based cells, and the production of high amounts of lentivirus. These methods allow for the production of cells that can be later induced to produce lentivirus, and can be tailored to include a specific gene of interest.

BACKGROUND OF THE INVENTION

Lentiviral vectors are one of the most commonly used delivery methods in the field of gene and cell therapy. In the process of lentiviral vector production, the sequences required for production of the vector are divided into several different plasmids or expression cassettes to minimize the chance of yielding a replication-competent lentivirus (RCL). In general, 3rd generation lentivirus production systems utilize four separate plasmids or expression cassettes that express:

1) Lentiviral group specific antigen (GAG) gene and a lentiviral polymerase (POL) protein;
2) Envelope protein (usually Vesicular Stomatitis Virus Glycoprotein (VSV-G));
3) HIV regulator of expression of virion proteins (Rev) protein; and
4) A Transfer vector (TV) containing a gene of interest (GOI).

In the most common approach, the above four plasmids are transiently transfected into cells to produce lentiviral vectors, which is labor-intensive and costly. In addition, transient transfection has a limitation in scalability as it requires large amounts of plasmid DNAs, which also raises a concern for safety.

What are needed to overcome difficulties associated with transient transfection, are methods for preparing a producer cell line (PCL), in which all or most of the genes or sequences required for lentiviral vector production are stably integrated into the chromosome of a mammalian cell allowing for the production of lentiviral vectors by a simple induction method. The present invention fulfills these needs.

SUMMARY OF THE INVENTION

In some embodiments, provided herein is method of producing a lentiviral packaging vector-containing mammalian cell, comprising: transfecting a mammalian cell with: a packaging vector including an expression cassette, encoding: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the expression cassette is flanked on both the 5' and 3' ends by transposon-specific inverted terminal repeats (ITR); and culturing the transfected mammalian cell; and isolating the lentiviral packaging vector-containing mammalian cell.

Also provided herein is a method of producing a lentiviral vector-producing mammalian cell, comprising: transfecting a mammalian cell with: a packaging vector including an expression cassette, encoding: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the expression cassette is flanked on both the 5' and 3' ends by transposon-specific inverted terminal repeats (ITR); and a transfer vector, comprising: a nucleic acid sequence encoding a gene of interest under control of a fourth promoter, wherein the nucleic acid sequence is flanked on both the 5' and 3' ends by transposon-specific inverted terminal repeats (ITR); culturing the transfected mammalian cell; and isolating the lentiviral vector-producing mammalian cell.

In further embodiments, provided herein is a method of producing a lentiviral vector, comprising: producing a lentiviral packaging vector-containing mammalian cell according to methods described herein; transfecting the mammalian cell with a transfer vector, comprising: a nucleic acid sequence encoding a gene of interest under control of a fourth promoter; inducing production of the expression cassette and the nucleic acid; culturing the transfected mammalian cell; and harvesting the lentiviral vector.

Also provided herein is a method of producing a lentiviral vector, comprising: producing a lentiviral vector-producing mammalian cell according to the methods described herein, inducing production of the expression cassette and the nucleic acid; culturing the mammalian cell; and harvesting the lentiviral vector.

In additional embodiments, provided herein is a method of treatment with a lentiviral vector, comprising: administering the lentiviral vector produced according to the methods described herein to a mammalian subject.

In further embodiments, provided herein is a mammalian cell for producing a lentiviral vector, comprising: a nucleic acid molecule chromosomally integrated into the mammalian cell, the nucleic acid molecule comprising a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the nucleic acid sequence is flanked on both the 5' and 3' ends by sequences resulting from the recombination of transposon-specific inverted terminal repeats (ITRs).

Also provided herein is a method of producing a lentiviral vector, comprising: transfecting the mammalian cells described herein with a transfer vector, comprising: an nucleic acid sequence encoding a gene of interest under control of a fourth promoter; inducing production of the expression cassette and the nucleic acid; culturing the transfected mammalian cell; and harvesting the lentiviral vector.

In further embodiments, provided herein is a method of producing a lentiviral vector, comprising: inducing production of the chromosomally integrated nucleic acid sequence and the chromosomally integrated nucleic acid sequence encoding a gene of interest of the mammalian cells described herein; culturing the mammalian cell; and harvesting the lentiviral vector.

DETAILED DESCRIPTION OF THE INVENTION

Figure 1:
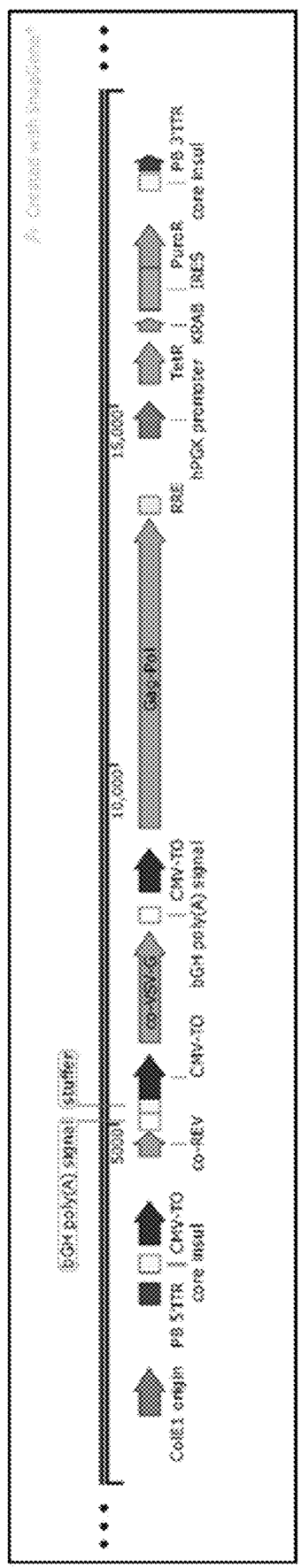
FIG. 1 shows a packaging plasmid in accordance with embodiments hereof.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer only to alternatives or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited, elements or method steps. It is contemplated that any embodiment discussed in this specification can be implemented with respect to any method, system, host cells, expression vectors, and/or composition of the invention. Furthermore, compositions, systems, cells, and/or nucleic acids of the invention can be used to achieve any of the methods as described herein.

As used herein, "nucleic acid," "nucleic acid molecule," or "oligonucleotide" means a polymeric compound comprising covalently linked nucleotides. The term "nucleic acid" includes polyribonucleic acid (RNA) and polydeoxyribonucleic acid (DNA), both of which may be single- or double-stranded. DNA includes, but is not limited to, complimentary DNA (cDNA), genomic DNA, plasmid or vector DNA, and synthetic DNA. RNA includes, but is not limited to, mRNA, tRNA, rRNA, snRNA, microRNA, miRNA, or MIRNA.

A "gene" as used herein refers to an assembly of nucleotides that encode a polypeptide, and includes cDNA and genomic DNA nucleic acid molecules. "Gene" also refers to a nucleic acid fragment that can act as a regulatory sequence preceding (5' non-coding sequences) and following (3' non-coding sequences) the coding sequence. In some embodiments, genes are integrated with multiple copies. In some embodiments, genes are integrated at predefined copy numbers.

Lentiviral Vectors and their Production

Lentiviral vector is a well studied vector system based on human immunodeficiency virus (HIV-1). Other lentiviral systems have also been developed as gene transfer systems, including HIV-2 simian immunodeficiency virus, nonprimate lentiviruses, feline immunodeficiency virus, and bovine immunodeficiency virus, etc. Guided by safety concerns due to the pathogenic nature of HIV-1 in humans, the most widely used lentiviral system for use in clinical and research and development purposes is based on the four-plasmid system that expresses:

1) Lentiviral group specific antigen (GAG) gene and a lentiviral polymerase (POL) protein
2) Envelope protein (usually Vesicular Stomatitis Virus Glycoprotein (VSV-G))
3) HIV regulator of expression of virion proteins (Rev) protein; and
4) A Transfer vector (TV) containing a gene of interest (GOI)

Traditionally, mammalian cells, such as human embryonic kidney cells (e.g., HEK293) are transfected with each of the four plasmids as an adherent cell culture, and then the desired lentivirus containing the gene of interest is produced. Generally, these transiently transfected cells are able to produce lentivirus.

Lentiviral vectors are generally produced with a gene of interest that is to be introduced into a desired cell for therapy and disease treatment, including immunodeficiencies and neurodegenerative diseases.

The present invention provides an improved methods of producing lentivirus, including methods for preparing lentivirus-producing cell lines that can be grown in suspension, allowing for a significant increase in the amount of lentivirus produced.

Lentiviral-Producing Cell Lines

In embodiments, provided herein is a method of producing a lentiviral packaging vector-containing mammalian cell. As used herein a "lentiviral packaging vector-containing cell" refers to a cell that contains, integrated into its genome, the elements required to produce a lentiviral vector, but that lacks a desired gene of interest that is to be carried by the lentiviral vector. Lentiviral packaging vector-containing cells can be later transfected with an e.g., transfer vector, that contains a desired gene of interest, and then subsequently induced to produce the desired lentivirus for ultimate delivery of the gene of interest.

Suitably, the cells that can be produced using the various methods described herein are mammalian cells and cell lines or cultures. As used herein, the term "mammalian cell" includes cells from any member of the order Mammalia, such as, for example, human cells, mouse cells, rat cells, monkey cells, hamster cells, and the like. In some embodiments, the cell is a mouse cell, a human cell, a Chinese hamster ovary (CHO) cell, a CHOK1 cell, a CHO-DXB11 cell, a CHO-DG44 cell, a CHOK1SV cell including all variants (e.g. POTELLIGENT®, Lonza, Slough, UK), a CHOK1SV GS-KO (glutamine synthetase knockout) cell including all variants (e.g., XCEED™ Lonza, Slough, UK). Exemplary human cells include human embryonic kidney (HEK) cells, such as HEK293, a HeLa cell, or a HT1080 cell.

Mammalian cells include mammalian cell cultures which can be either adherent cultures or suspension cultures. Adherent cultures refer to cells that are grown on a substrate surface, for example a plastic plate, dish or other suitable cell culture growth platform, and may be anchorage dependent. Suspension cultures refer to cells that can be maintained in, for example, culture flasks or large suspension vats, which allows for a large surface area for gas and nutrient exchange. Suspension cell cultures often utilize a stirring or agitation mechanism to provide appropriate mixing. Media and conditions for maintaining cells in suspension are generally known in the art. An exemplary suspension cell culture includes human HEK293 clonal cells.

In embodiments, the methods described herein include transfecting a mammalian cell with a packaging vector including an expression cassette. As used herein, a "vector" or "expression vector" is a replicon, such as a plasmid, phage, virus, or cosmid, to which a nucleic acid molecule described herein may be attached to bring about the replication and/or expression of the attached nucleic acid molecule in a cell. "Vector" includes episomal (e.g., plasmids) and non-episomal vectors. The term "vector" includes both viral and nonviral means for introducing a nucleic acid molecule into a cell in vitro, in vivo, or ex vivo. The term vector may include synthetic vectors. Vectors may be introduced into the desired host cells by well-known methods, including, but not limited to, transfection, transduction, cell fusion, and lipofection. Vectors can comprise various regulatory elements including promoters.

"Transfection" as used herein means the introduction of an exogenous nucleic acid molecule, including a vector, into a cell. A "transfected" cell comprises an exogenous nucleic acid molecule inside the cell and a "transformed" cell is one in which the exogenous nucleic acid molecule within the cell induces a phenotypic change in the cell. The transfected nucleic acid molecule can be integrated into the host cell's genomic DNA and/or can be maintained by the cell, temporarily or for a prolonged period of time, extra-chromosomally. Host cells or organisms that express exogenous nucleic acid molecules or fragments are referred to as "recombinant," "transformed," or "transgenic" organisms. A number of transfection techniques are generally known in the art. See, e.g., Graham et al., *Virology*, 52:456 (1973); Sambrook et al., Molecular Cloning, a laboratory manual, Cold Spring Harbor Laboratories, New York (1989); Davis et al., Basic Methods in Molecular Biology, Elsevier (1986); and Chu et al., *Gene* 13:197 (1981). Suitably, transfection of a mammalian cell with one or more of the vectors described herein utilizes a transfection agent, such as polyethylenimine (PEI) or other suitable agent, including various lipids and polymers, to integrate the nucleic acids into the host cell's genomic DNA.

As used herein, a "packaging vector" refers to a vector that contains the components necessary to produce a lentiviral vector and "package" a gene of interest in the final, lentivirus. The packaging vector includes an expression cassette, which refers to a distinct component of a vector, and includes one or more genes and regulatory sequences to be inserted into, and ultimately expressed by, a transfected cell.

Suitably, the expression cassette used in the packaging vector includes a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter. In other embodiments, a single promoter can control the expression of each of the REV, ENV, GAG and POL genes, or one promoter can control expression of GAG and POL, and a second promoter control the expression or REV and ENV. Other combinations are also possible and included herein.

The lentiviral regulator of expression of virion proteins (REV) is an RNA-binding protein that promotes late phase gene expression. It is also important for the transport of the unspliced or singly-spliced mRNAs, which encode viral structural proteins, from the nucleus to the cytoplasm.

The lentiviral envelope (ENV) gene, suitably a Vesicular Stomatitis Virus Glycoprotein (VSV-G) gene, encodes a polyprotein precursor which is cleaved by a cellular protease into the surface (SU) envelope glycoprotein gp120 and the transmembrane (TM) glycoprotein gp41.

GAG encodes a polyprotein that is translated from an unspliced mRNA which is then cleaved by the viral protease (PR) into the matrix protein, capsid, and nucleocapsid proteins. The lentiviral polymerase (POL) is expressed as a GAG-POL polyprotein as a result of ribosomal frameshifting during GAG mRNA translation, and encodes the enzymatic proteins reverse transcriptase, protease, and integrase. These three proteins are associated with the viral genome within the virion. Suitably the GAG gene is an HIV GAG gene and the POL gene is an HIV POL gene.

In suitable embodiments, the expression cassette is flanked on both the 5' and 3' ends by transposon-specific inverted terminal repeats (ITR). As described in detail herein, it is the use of transposon ITRs (in combination with a corresponding transposase) that allow for the specific integration of the expression cassette into the genome of the target cell.

The methods for producing the lentiviral packaging vector-containing mammalian cell further comprise culturing the transfected mammalian cell to allow for integration of the desired nucleic acids (i.e., the expression cassette) into the genome of the cell, followed by isolating the lentiviral packaging vector-containing mammalian cell.

Methods for culturing the transfected mammalian cell are known in the art and include the use of various cell culture media, appropriate gas concentration/exchange and temperature control to promote growth of the cells and integration of the constructs into the genome of the cell.

Methods of isolating the desired cells include various filtration techniques, including the use of sieves, filter apparatus, cell-selection apparatus and sorting, cell counting, etc.

As noted herein, each of the components of the expression cassette are under the control of a promoter. As used herein "under control" refers to a gene being regulated by a "promoter," "promoter sequence," or "promoter region," which refers to a DNA regulatory region/sequence capable of binding RNA polymerase and initiating transcription of a downstream coding or non-coding gene sequence. In other words, the promoter and the gene are in operable combination or operably linked. As referred to herein, the terms "in operable combination", "in operable order" and "operably linked" refer to the linkage of nucleic acid sequences in such a manner that a promoter capable of directing the transcription of a given gene and/or the synthesis of a desired protein molecule is produced. The term also refers to the linkage of amino acid sequences in such a manner so that a functional protein is produced.

In some examples of the present disclosure, the promoter sequence includes the transcription initiation site and extends upstream to include the minimum number of bases or elements necessary to initiate transcription at levels detectable above background. In some embodiments, the promoter sequence includes a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the gene expression, e.g., in the host cell or vectors of the present disclosure. In some embodiments, the promoter is not a leaky promoter, i.e., the promoter is not constitutively expressing any of the gene products as described herein. In other embodiments as described herein, the promoter is a constitutive promoter, which initiates mRNA synthesis independent of the influence of an external regulation.

Suitably, the promoters used to control the transcription of the various genes in the expression cassettes are derepressible promoters. As used herein, a "derepressible promoter" refers to a structure that includes a functional promoter and additional elements or sequences capable of binding to a repressor element to cause repression of the functional promoter. "Repression" refers to the decrease or inhibition of the initiation of transcription of a downstream coding or non-coding gene sequence by a promoter. A "repressor element" refers to a protein or polypeptide that is capable of binding to a promoter (or near a promoter) so as to decrease or inhibit the activity of the promoter. A repressor element can interact with a substrate or binding partner of the repressor element, such that the repressor element undergoes a conformation change. This conformation change in the repressor element takes away the ability of the repressor element to decrease or inhibit the promoter, resulting in the "derepression" of the promoter, thereby allowing the promoter to proceed with the initiation of transcription. A "functional promoter" refers to a promoter, that absent the action of the repressor element, would be capable of initiation transcription. Various functional promoters that can be used in the practice of the present invention are known in the art, and include for example, PCMV, PH1, P19, P5, P40 and promoters of Adenovirus helper genes (e.g., E1A, E1B, E2A, E4Orf6, and VA).

Exemplary repressor elements and their corresponding binding partners that can be used as derepressible promoters are known in the art, and include systems such as the cumate gene-switch system (CuO operator, CymR repressor and cumate binding partner) (see, e.g., Mullick et al., "The cumate gene-switch: a system for regulated expression in mammalian cells," BMC Biotechnology 6:43 (1-18) (2006), the disclosure of which is incorporated by reference herein in its entirety, including the disclosure of the derepressible promoter system described therein) and the TetO/TetR system described herein (see, e.g., Yao et al., "Tetracycline Repressor, tetR, rather than the tetR-Mammalian Cell Transcription Factor Fusion Derivatives, Regulates Inducible Gene Expression in Mammalian Cells," Human Gene Therapy 9:1939-1950 (1998), the disclosure of which is incorporated by reference herein in its entirety). In exemplary embodiments, the derepressible promoters comprise a functional promoter and either one two tetracycline operator sequences (TetO or TetO$_2$). Suitably, the expression cassette further encodes a repressor element of the first, second and third derepressible promoters, including a tetracycline repressor protein.

A schematic showing a depressible promoter system is provided in FIG. 1, illustrating an exemplary packaging plasmid in accordance with embodiments hereof. A derepressible promoter including the CMV promoter, including a TetO sequence is noted (CMV-TO). CMV-TO depressible promoters are illustrated operably linked to REV, VSV-G and GAG-POL genes; that is the first, second and third promoters can all be derepressible promoters, in suitable embodiments. Also illustrated is the TetR repressor element, under the control of another promoter system, the hPGK promoter.

Upon binding of a tetracycline repressor protein (TetR—the repressor elements for the TetO sequences), to the TetO sequences, the CMV promoters are repressed. That is, little or no transcription takes place from these promoters. Upon binding of a binding partner for TetR (suitably Doxycycline (Dox)), the TetR proteins change conformation, release from the TetO sequences, and the functional promoters begin their normal transcription processes, as they would naturally.

As shown in FIG. 1, the expression cassette can further include a Kruppel-associated box (KRAB) sequence following the sequence encoding the repressor element, suitably the tetracycline repressor protein. A KRAB sequence (approximately 75 amino acids) is a transcriptional repression domain from the human zinc finger protein 10, and provides increased regulation of the repressor element, suitably the TetR repressor element. The KRAB domain functions as a transcriptional repressor when tethered to the template DNA by a DNA-binding domain. Also illustrated are exemplary locations of the 5' and 3' ITR transposon sequences. As noted, the ITR sequences are located such that the entirety of the expression cassette is transposed into the cell of interest, allowing for all of the desired genes to be inserted into the host genome.

In exemplary embodiments, the expression cassette further includes one or more reporter genes for determining the appropriate integration of the cassette into the genome of the cell. As referred to herein, a "reporter gene" is a gene whose expression confers a phenotype upon a cell that can be easily identified and measured. In some embodiments, the reporter gene comprises a fluorescent protein gene. In some embodiments, the reporter gene comprises a selection gene. As referred to herein, the term "selection gene" refers to the use of a gene which encodes an enzymatic activity that confers the ability to grow in medium lacking what would otherwise be an essential nutrient; in addition, a selection gene may confer resistance to an antibiotic or drug upon the cell in which the selection gene is expressed. A selection gene may be used to confer a particular phenotype upon a host cell. When a host cell must express a selection gene to grow in selective medium, the gene is said to be a positive selection gene. A selection gene can also be used to select against host cells containing a particular gene; a selection gene used in this manner is referred to as a negative selection gene. In exemplary embodiments the selection gene is placed downstream of KRAB sequence following the repressor protein, and also downstream of an internal ribosome entry site (IRES) sequence. In exemplary embodiments, the selection gene is an antibiotic resistance gene, including for example a gene that confers resistance to gentamycin, thymidine kinase, ampicillin, puromycin, and/or kanamycin.

As described in detail herein, it has been determined that the use of transposon-specific ITRs allow for the insertion of the expression cassette into the genome of a target cell with increased specificity, frequency and stability. In exemplary embodiments, the transposon-specific ITRs are Lepidopteran transposon (PIGGYBAC®) ITRs.

Transposable elements (transposons) can move around a genome of a cell and are useful for inserting genes for the production of transgenic organisms. The Lepidopteran transposon PIGGYBAC® is capable of moving within the genomes of a wide variety of species, and is useful in gene transduction vectors. The transposon structure includes a complex repeat configuration consisting of an internal repeat (IR), a spacer, and a terminal repeat (TR) at both ends, and a single open reading frame encoding a transposase.

The Lepidopteran transposable element PIGGYBAC® was originally isolated from the TN-368 *Trichoplusia ni* cell culture as a gene disrupting insertion within spontaneous baculovirus plaque morphology mutants. PIGGYBAC® is a 2475 bp short inverted repeat element that has an asymmetric terminal repeat structure with a 3-bp spacer between the 5' 13-bp TR (terminal repeat) and the 19-bp IR (internal repeat), and a 31-bp spacer between the 3' TR and IR. The single 2.1 kb open reading frame encodes a functional transposase (Cary et al., 1989; Fraser et al., 1983, 1995; Elick et al., 1996a; Lobo et al., 1999; Handler et al., 1998). PIGGYBAC® transposes via a unique cut-and-paste mechanism, inserting exclusively at 5' TTAA 3' target sites that are duplicated upon insertion, and excising precisely, leaving no footprint (Elick et al., 1996b; Fraser et al., 1996; Wang and Fraser 1993).

Exemplary Lepidopteran transposon (PIGGYBAC®) ITRs that can be used in the plasmids and expression cassettes described herein include those disclosed in U.S. Pat. No. 7,105,343, the disclosure of which is incorporated by reference herein in its entirety.

In suitable embodiments, transfecting of the mammalian cells with the packaging vector takes place in the presence of a transposase that recognizes the transposon-specific ITRs. This transposase facilitates the transposition of the expression cassette into the cellular genome of the target mammalian cell. Transposase can be provided to the cell either as an active enzyme, or as a nucleic acid sequence that encodes the transposase, including mRNA or cDNA. In embodiments, the transposase is Lepidopteran (PIGGYBAC®) transposase mRNA or Lepidopteran (PIGGYBAC®) transpose cDNA. As described herein, the frequency of the transposition utilizing Lepidopteran transposon (PIGGYBAC®) ITRs and corresponding Lepidopteran (PIGGYBAC®) transposase is suitably at least about 10-4.

In further embodiments, provided herein are methods of producing a lentiviral vector-producing mammalian cell. As used herein a "lentiviral vector-producing cell" refers to a cell that contains, integrated into its genome, the elements required to produce a lentiviral vector, as well a desired gene of interest that is to be carried by the lentiviral vector. Lentiviral vector-producing cells can be later induced to produce the desire lentivirus for ultimate delivery of the gene of interest.

Methods producing a lentiviral vector-producing cell, and in particular mammalian cells, include transfecting a mammalian cell with: packaging vector including an expression cassette, encoding: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter.

As described herein the expression cassette is suitably flanked on both the 5' and 3' ends by transposon-specific inverted terminal repeats (ITR) to facilitate high transposition into the target cell.

The methods further include transecting the mammalian cell with a transfer vector, comprising: a nucleic acid sequence encoding a gene of interest under control of a fourth promoter. As with the expression cassette, the nucleic acid sequence encoding the gene of interest is also suitably flanked on both the 5' and 3' ends by transposon-specific inverted terminal repeats (ITR) for increased transposition. In embodiments both the transfer vector and the packaging vector are transfected at the same time; in other embodiments, the transfer vector or the packaging vector can be transfected first, with the other vector transfected at a later time.

Following the transfection, the mammalian cell is cultured, and the lentiviral vector-producing mammalian cell is isolated.

As with the lentiviral packaging vector-containing cells, lentiviral vector-producing cells prepared herein are suitably stored prior to the desired time at which they can be utilized to produce lentiviral vectors. Suitable storage techniques and characteristics are known in the art and can include refrigeration or freezing of cells, as well as other methods of maintaining the cells in a suspended state prior to induction of the vector production.

As described herein, suitably the mammalian cell is a mammalian cell culture, and in embodiments is a suspension culture. Exemplary cells include HEK293T cells.

As in the lentiviral packaging vector-containing cells, the genes of the expression vector suitably include a GAG gene that is an HIV GAG gene and a POL gene that is an HIV POL gene. Suitably, the lentiviral envelope gene is a Vesicular Stomatitis Virus Glycoprotein (VSV-G) gene.

Exemplary promoters for use in the lentiviral vector-producing cells are known in the art and include derepressible promoters, and suitably the expression cassette further encodes a repressor element of the first, second and third derepressible promoters. In embodiments, the derepressible promoters comprises a functional promoter and a tetracycline operator sequence (TetO), and the repressor element is a tetracycline repressor protein. Additional characteristics of the expression cassette, including the transposon-specific ITRs are described herein.

In suitable embodiments, the gene of interest that is to be contained in the lentiviral vector is a gene of therapeutic interest. As referred to herein, the term "gene of interest" or "GOI" is used to describe a heterologous gene. As referred to herein, the term "heterologous gene" or "HG" as it relates to nucleic acid sequences such as a coding sequence or a control sequence, denotes a nucleic acid sequence, e.g. a gene, that is not normally joined together, and/or are not normally associated with a particular cell. In some embodiments, a heterologous gene is a construct where the coding sequence itself is not found in nature (e.g., synthetic sequences having codons different from the native gene). Allelic variation or naturally occurring mutational events do not give rise to heterologous DNA, as used herein.

As referred to herein, the term "gene of therapeutic interest" refers to any functionally relevant nucleotide sequence. Thus, the gene of therapeutic interest of the present disclosure can comprise any desired gene that encodes a protein that is defective or missing from a therapy-target cell genome or that encodes a non-native protein having a desired biological or therapeutic effect (e.g., an antiviral function), or the sequence can correspond to a molecule having an antisense or ribozyme function. Representative (non-limiting) examples of suitable genes of therapeutic interest include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc. Several antisense oligonucleotides (e.g., short oligonucleotides complementary to sequences around the translational initiation site (AUG codon) of an mRNA) that are useful in antisense therapy for cancer and for viral diseases have been described in the art and are also examples of suitable genes of therapeutic interest.

Figure 2:
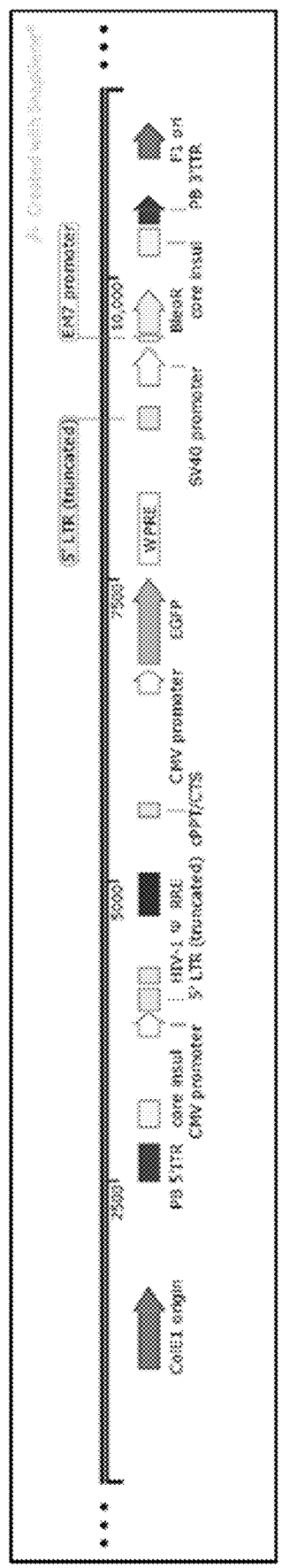
FIG. 2 shows a transfer vector in accordance with embodiments hereof.
Figure 3:
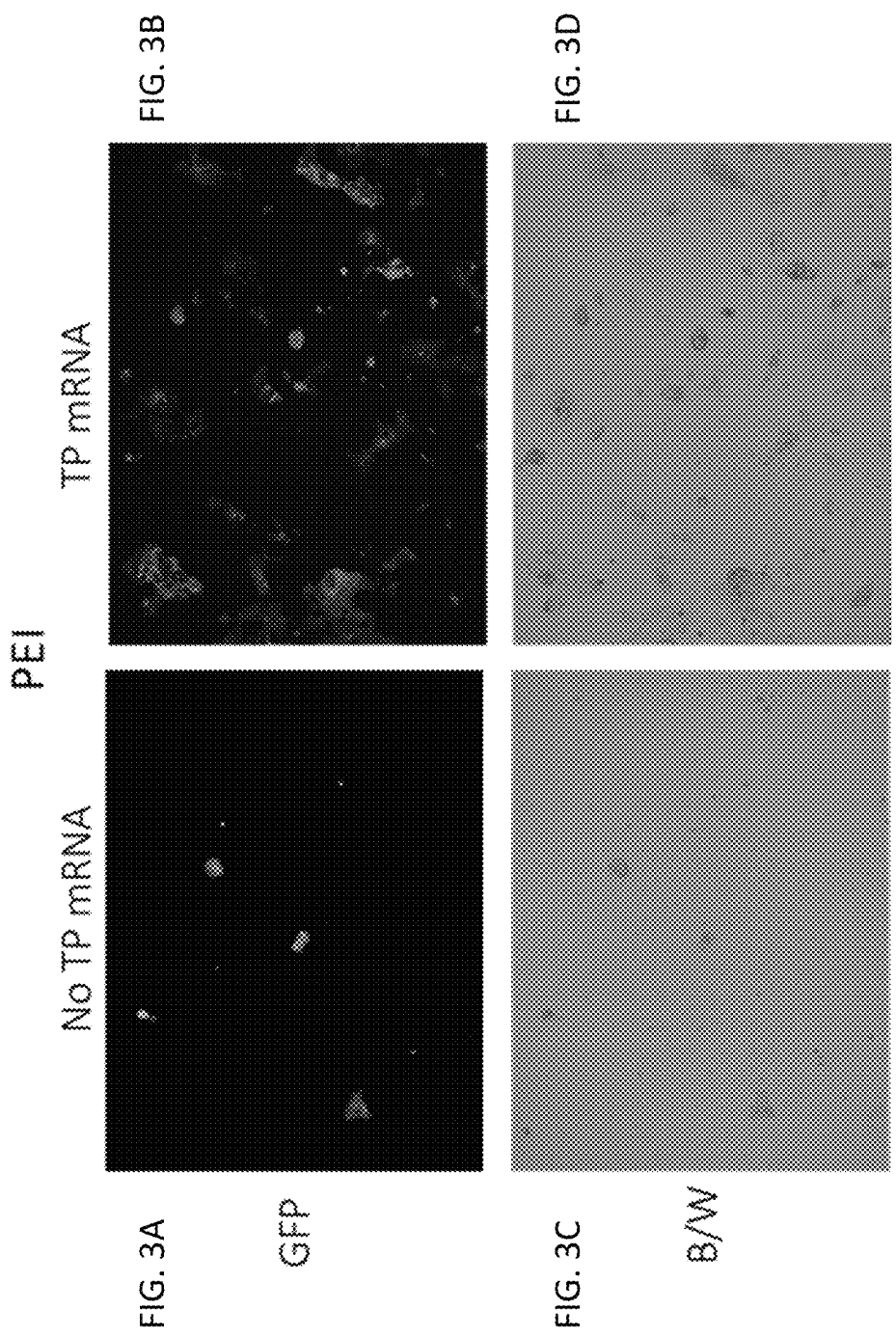
FIGS. 3A-3D show HEK293T cells transfected with packaging and transfer vectors, in accordance with embodiments hereof.

FIG. 2 shows an exemplary transfer vector that includes a gene of interest (enhanced green fluorescent protein for illustrative purposes). The gene of interest is under the control of a promoter, suitably a constitutive promoter, in this case a CMV promoter. Also illustrated are exemplary locations for the 5' and 3' ITR transposon sequences. As noted, the ITR sequences are located such that the entirety of the nucleic acid that contains the gene of interest and the promoter is transposed into the cell of interest, allowing for all of the desired genes to be inserted into the host genome. As indicated, the exemplary transfer vector also includes a selection gene, in this case a bleomycin resistance gene, downstream of the gene of interest. Additional elements of the transfer vector are shown in FIG. 2.

In additional embodiments, provided herein is a method of producing a lentiviral vector, comprising producing or providing a lentiviral packaging vector-containing mammalian cell as described herein, then transfecting the mammalian cell with a transfer vector, comprising a nucleic acid sequence encoding a gene of interest under control of a fourth promoter. Following the introduction of the gene of interest into the cellular genome, the production of the expression cassette and the nucleic acid encoding the gene of interest are induced. The cells are then cultured, and finally the lentiviral vector containing the gene of interest is harvested.

In still further embodiments, methods of producing a lentiviral vector suitably include producing or providing a lentiviral vector-producing mammalian cell as described herein. The production of the expression cassette and the nucleic acid encoding the gene of interest are induced. The cells are then cultured, and finally the lentiviral vector containing the gene of interest is harvested.

The methods of producing lentiviral vector using the cells described herein, whether they contain simply the lentiviral packaging vector, or also contain the gene of interest, integrated into the cellular genome, provide a mechanism for generation of large amounts of lentiviral vector, as well as controlling when the induction begins and the conditions under which the induction takes place. Induction suitably comprises the introduction of a chemical or agent that interacts with the repressor element, thereby derepressing the derepressible promoter, and allowing production of the packaging components of the lentiviral vector.

As described herein, suitably each of the promoters in the expression cassette is a derepressible promoter comprising a functional promoter and a tetracycline operator sequence (TetO), and the repressor element is a tetracycline repressor protein. In such embodiments, induction of packing components includes adding doxycycline to the mammalian cell.

The methods described herein provide for an increased amount of production of lentiviral vector, as a result of the increase in insertion of the desired nucleic acid sequences into the cellular genome and the suspension-based cell culture allowing for large volume production. In embodiments, the amount of the lentiviral vector produced is at least about 104, more suitably about $10^5$ or about $10^6$ transduction units/mL, within about 1-5 days, suitably about two days after the inducing of the cells.

Production methods using the cells described herein can utilize any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermenter or fermentation unit, or any other reaction vessel and the term "reactor" is used interchangeably with "fermenter." The term fermenter or fermentation refers to both microbial and mammalian cultures. For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

As described herein, it has been surprisingly determined that at least portions of the methods for producing lentivirus using producing cells lines can be carried out in the absence of antibiotics, including seed train production, cell passages, large volume cell culture and/or main manufacturing stages. By removing antibiotics from at least a portion of the lentivirus production process, the resulting methods reduce or remove concerns related to the use of antibiotics in cell processes and products that will ultimately be utilized in humans.

Figure 10:
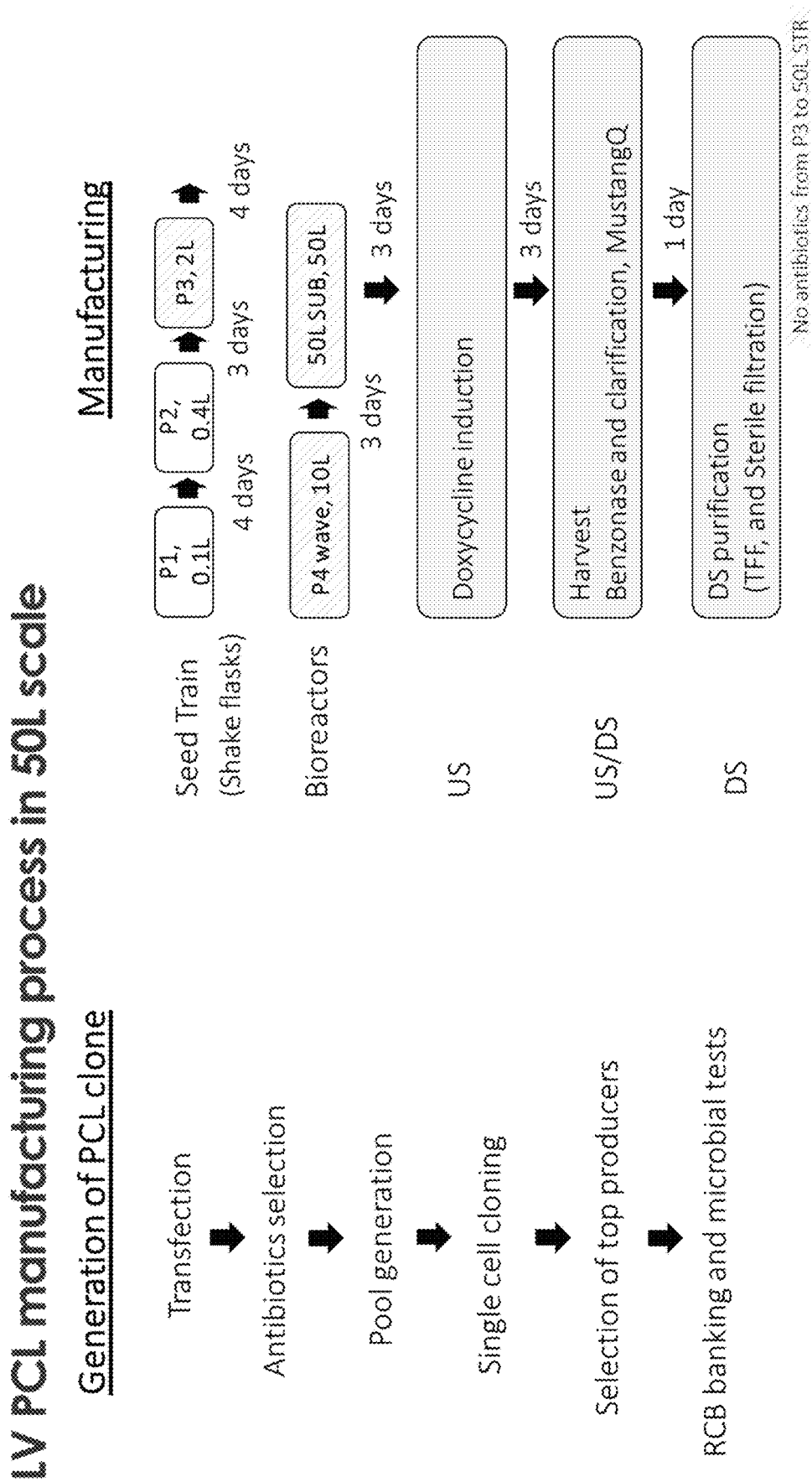
FIG. 10 shows an exemplary manufacturing flow for lentivirus PCL without antibiotics during parts of a seed train culture.

FIG. 10 shows an exemplary manufacturing process flow for preparing lentivirus from producer cell lines as described herein. As shown, PCL clones are first generated, and then selected for use in a large scale manufacturing process. During initial stages of the manufacturing process, the PCLs are passaged up to about 3 times (e.g., a volume of about 2 L), at which time antibiotics such as puromycin and/or zeocin, can be removed from the process. The passages can then be continued in the absence of antibiotic, for example from passage 3, passage 4, passage 5, etc., until the desired volume of cells is reached. For example, as shown in FIG. 10, suitably a volume of about 50 L is reached in a bioreactor, in the absence of an antibiotic. The PCLs are then suitably induced (e.g., using doxycycline as described herein) to begin the production of the lentiviral vector. Thus, in embodiments, a at least a portion of the culturing of the mammalian cells (PCLs) occurs in the absence of an antibiotic, and suitably this period is from passage 3 up to an induction phase. Following induction, downstream processing can take place, including harvesting (including benzonase treatment and clarification steps) and purification of the lentiviral vector (including tangential flow filtration and sterile filtration). The ability to carry out significant portions of the lentiviral vector production process using PCLs as described herein is a surprising and unexpected result and provides significant advantages to large scale manufacturing processes.

Also provided herein are methods of treating a mammalian subject, suitably a human subject, with a lentiviral vector produced according to the various methods described herein. Suitably, the methods are used to treat a human subject with a gene of interested, including a gene of therapeutic interest. Administration to a human subject can include, for example, inhalation, injection, or intravenous administration, as well as other administration methods known in the art.

Also provided herein are mammalian cells for producing a lentiviral vector. Using the methods described herein, or variations thereof, mammalian cells are readily produced that include a nucleic acid molecule chromosomally integrated into the mammalian cell, the nucleic acid molecule comprising a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter. In further embodiments, mammalian cells containing the packaging components integrated into the genome can further include a chromosomally integrated nucleic acid sequence encoding a gene of interest under control of a fourth promoter.

As described herein, the use of transposase-based methods, including PIGGYBAC® transposase, results in the nucleic acid sequence in the host cell genome being flanked on both the 5' and 3' ends by sequences resulting from the recombination of transposon-specific inverted terminal repeats (ITRs).

Exemplary mammalian cells are described herein, as are the gene components of the expression cassette and the nucleic acid encoding the gene of interest.

Methods of producing lentivirus utilizing these cells are described herein, and suitably include inducing production of the expression cassette and the nucleic acid encoding the gene of interest, culturing the transfected mammalian cell, and harvesting the lentiviral vector.

ADDITIONAL EXEMPLARY EMBODIMENTS

Embodiment 1 is a method of producing a lentiviral packaging vector-containing mammalian cell, comprising: transfecting a mammalian cell with: a packaging vector including an expression cassette, encoding: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the expression cassette is flanked on both the 5' and 3' ends by transposon-specific inverted terminal repeats (ITR); and culturing the transfected mammalian cell; and isolating the lentiviral packaging vector-containing mammalian cell.

Embodiment 2 includes the method of embodiment 1, wherein the mammalian cell is a mammalian cell culture.

Embodiment 3 includes the method of embodiment 2, wherein the mammalian cell culture is a suspension culture.

Embodiment 4 includes the method of embodiment 3, wherein the mammalian cell is an HEK293T cell.

Embodiment 5 includes the method of any one of embodiments 1-4, wherein the GAG gene is an HIV GAG gene and the POL gene is an HIV POL gene.

Embodiment 6 includes the method of any one of embodiments 1-5, wherein the lentiviral envelope gene is a Vesicular Stomatitis Virus Glycoprotein (VSV-G) gene.

Embodiment 7 includes the method of any one of embodiments 1-6, wherein the first, second and third promoters are derepressible promoters.

Embodiment 8 includes the method of embodiment 7, wherein the expression cassette further encodes a repressor element of the first, second and third derepressible promoters Embodiment 9 includes the method of embodiment 8, wherein each of the derepressible promoters comprises a functional promoter and a tetracycline operator sequence (TetO), and the repressor element is a tetracycline repressor protein.

Embodiment 10 includes the method of embodiment 9, wherein the expression cassette further comprises a Kruppel-associated box sequence following a sequence encoding the tetracycline repressor protein.

Embodiment 11 includes the method of any one of embodiments 1-10, wherein the transposon-specific ITRs are Lepidopteran transposon (PIGGYBAC®) ITRs.

Embodiment 12 includes the method of any one of embodiments 1-11, wherein the transfecting is in the presence of a transposase that recognizes the transposon-specific ITRs.

Embodiment 13 includes the method of embodiment 12, wherein the transposase is Lepidopteran (PIGGYBAC®) transposase mRNA or Lepidopteran (PIGGYBAC®) transpose cDNA.

Embodiment 14 is a method of producing a lentiviral vector-producing mammalian cell, comprising: transfecting a mammalian cell with: a packaging vector including an expression cassette, encoding: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the expression cassette is flanked on both the 5' and 3' ends by transposon-specific inverted terminal repeats (ITR); and a transfer vector, comprising: a nucleic acid sequence encoding a gene of interest under control of a fourth promoter, wherein the nucleic acid sequence is flanked on both the 5' and 3' ends by transposon-specific inverted terminal repeats (ITR); culturing the transfected mammalian cell; and isolating the lentiviral vector-producing mammalian cell.

Embodiment 15 includes the method of embodiment 14, wherein the mammalian cell is a mammalian cell culture.

Embodiment 16 includes the method of embodiment 15, wherein the mammalian cell culture is a suspension culture.

Embodiment 17 includes the method of embodiment 16, wherein the mammalian cell is an HEK293T cell.

Embodiment 18 includes the method of any one of embodiments 14-17, wherein the GAG gene is an HIV GAG gene and the POL gene is an HIV POL gene.

Embodiment 19 includes the method of any one of embodiments 14-18, wherein the lentiviral envelope gene is a Vesicular Stomatitis Virus Glycoprotein (VSV-G) gene.

Embodiment 20 includes the method of any one of embodiments 14-19, wherein the first, second and third promoters are derepressible promoters.

Embodiment 21 includes the method of embodiment 20, wherein the expression cassette further encodes a repressor element of the first, second and third derepressible promoters Embodiment 22 includes the method of embodiment 21, wherein each of the derepressible promoters comprises a functional promoter and a tetracycline operator sequence (TetO), and the repressor element is a tetracycline repressor protein.

Embodiment 23 includes the method of embodiment 22, wherein the expression cassette further comprises a Kruppel-associated box sequence following a sequence encoding the tetracycline repressor protein.

Embodiment 24 includes the method of any one of embodiments 14-23, wherein the transposon-specific ITRs are Lepidopteran transposon (PIGGYBAC®) ITRs.

Embodiment 25 includes the method of any one of embodiments 14-24, wherein the transfecting is in the presence of a transposase that recognizes the transposon-specific ITRs.

Embodiment 26 includes the method of embodiment 25, wherein the transposase is Lepidopteran (PIGGYBAC®) transposase mRNA or Lepidopteran (PIGGYBAC®) transpose cDNA.

Embodiment 27 includes the method of any one of embodiments 14-26, wherein the gene of interest is a gene of therapeutic interest.

Embodiment 28 is a method of producing a lentiviral vector, comprising: producing a lentiviral packaging vector-containing mammalian cell according to embodiment 1; transfecting the mammalian cell with a transfer vector, comprising: a nucleic acid sequence encoding a gene of interest under control of a fourth promoter; inducing production of the expression cassette and the nucleic acid; culturing the transfected mammalian cell; and harvesting the lentiviral vector.

Embodiment 29 is a method of producing a lentiviral vector, comprising: producing a lentiviral vector-producing mammalian cell according to embodiment 14; inducing production of the expression cassette and the nucleic acid; culturing the mammalian cell; and harvesting the lentiviral vector.

Embodiment 30 includes the method of embodiment 28 or embodiment 29, wherein each of the promoters in the expression cassette is a derepressible promoter comprising a functional promoter and a tetracycline operator sequence (TetO), and the repressor element is a tetracycline repressor protein, and the inducing includes adding doxycycline to the mammalian cell.

Embodiment 31 includes the method of embodiment 28 or embodiment 29, wherein an amount of the lentiviral vector produced is at least about $10^6$ transduction units/mL two days after the inducing.

Embodiment 32 is a method of treatment with a lentiviral vector, comprising: administering the lentiviral vector produced according to embodiment 28 or embodiment 29 to a mammalian subject.

Embodiment 33 includes the method of embodiment 32, wherein the administering comprises inhalation, injection or intravenous administration.

Embodiment 34 is a mammalian cell for producing a lentiviral vector, comprising: a nucleic acid molecule chromosomally integrated into the mammalian cell, the nucleic acid molecule comprising a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the nucleic acid sequence is flanked on both the 5' and 3' ends by sequences resulting from the recombination of transposon-specific inverted terminal repeats (ITRs).

Embodiment 35 includes the mammalian cell of embodiment 34, further comprising a chromosomally integrated nucleic acid sequence encoding a gene of interest under control of a fourth promoter.

Embodiment 36 includes the mammalian cell of embodiment 34 or embodiment 35, wherein the mammalian cell is a mammalian cell culture.

Embodiment 37 includes the mammalian cell of embodiment 36, wherein the mammalian cell culture is a suspension culture.

Embodiment 38 includes the mammalian cell of embodiment 37, wherein the mammalian cell is an HEK293T cell.

Embodiment 39 includes the mammalian cell of any one of embodiments 34-38, wherein the GAG gene is an HIV GAG gene and the POL gene is an HIV POL gene.

Embodiment 40 includes the mammalian cell of any one of embodiments 34-39, wherein the lentiviral envelope gene is a Vesicular Stomatitis Virus Glycoprotein (VSV-G) gene.

Embodiment 41 includes the mammalian cell of any one of embodiments 34-40, wherein the first, second and third promoters are derepressible promoters.

Embodiment 42 includes the mammalian cell of embodiment 41, wherein the expression cassette further encodes a repressor element of the first, second and third derepressible promoters Embodiment 43 includes the mammalian cell of embodiment 42, wherein each of the derepressible promoters comprises a functional promoter and a tetracycline operator sequence (TetO), and the repressor element is a tetracycline repressor protein.

Embodiment 44 includes the mammalian cell of embodiment 43, wherein the expression cassette further comprises a Kruppel-associated box sequence following a sequence encoding the tetracycline repressor protein.

Embodiment 45 includes the mammalian cell of any one of embodiments 34-44, wherein the transposon-specific ITRs are Lepidopteran transposon (PIGGYBAC®) ITRs.

Embodiment 46 includes the mammalian cell of embodiment 35, wherein the gene of interest is a gene of therapeutic interest.

Embodiment 47 is a method of producing a lentiviral vector, comprising: transfecting the mammalian cell of embodiment 34 with a transfer vector, comprising: a nucleic acid sequence encoding a gene of interest under control of a fourth promoter; inducing production of the expression cassette and the nucleic acid; culturing the transfected mammalian cell; and harvesting the lentiviral vector.

Embodiment 48 is a method of producing a lentiviral vector, comprising: inducing production of the chromosomally integrated nucleic acid sequence and the chromosomally integrated nucleic acid sequence encoding a gene of interest of the mammalian of embodiment 35; culturing the mammalian cell; and harvesting the lentiviral vector.

Embodiment 49 includes the method embodiment 47 or embodiment 48, wherein each of the promoters in the expression cassette is a derepressible promoter comprising a functional promoter and a tetracycline operator sequence (TetO), and the repressor element is a tetracycline repressor protein, and the inducing includes adding doxycycline to the mammalian cell.

Embodiment 50 includes the method embodiment 47 or embodiment 48, wherein an amount of the lentiviral vector produced is at least about $10^6$ transduction units/mL two days after the inducing.

Embodiment 51 is a method of treatment with a lentiviral vector, comprising: administering the lentiviral vector produced according to embodiment 47 or embodiment 48 to a mammalian subject.

Embodiment 52 includes the method of embodiment 51, wherein the administering comprises inhalation, injection or intravenous administration.

Embodiment 53 includes the methods of any of embodiments 28-31 and 47-50, wherein at least a portion of the culturing the mammalian cell occurs in the absence of an antibiotic.

Embodiment 54 includes the method of embodiment 53, wherein the portion of the culturing is from passage 3 up to an induction phase.

EXAMPLES

Example 1: Design and Construction of Lentiviral Producer Cell Line

Materials and Methods

To construct a lentiviral producer cell line, two plasmids were designed:
1) A packaging plasmid that expresses GAG-Pol, VSV-G, and Rev in a regulated fashion; and
2) A transfer vector that expresses a gene of interest.

The coding sequence for VSV-G, and Rev is codon-optimized (co) as codon optimization has been proven as one of the most effective ways to increase the protein synthesis without changing the actual amino acid sequence of proteins.

The sequence encoding GAG-Pol is not codon-optimized. All these sequences are put under the control of CMV-TO promoter, the activity of which is repressed in the absence of tetracycline or doxycycline by TetR. In our design, the sequence of Kruppel-associated box (KRAB), which is a transcriptional repression domain from the human zinc finger protein 10, was inserted right after the TetR coding sequence to achieve more tight regulation of CMV-TO.

Addition of doxycycline, upon its binding to TetR, induces a conformation change in TetR to release TetR from CMV-TO. As a result, CMV-TO becomes active and expresses VSV-G, Rev, and GAG-Pol. The regulated expression of VSV-G, Rev, and GAG-Pol minimizes any cytotoxicity associated with these proteins and also, keeps the lentiviral vector production in a basal level before any induction. In order to facilitate the selection process, an antibiotic resistance marker (puromycin) was introduced into this plasmid downstream of the IRES sequence, which was placed right after KRAB sequence. Therefore, human phosphoglycerate promoter drives the expression of TetR-KRAB and puromycin resistance gene altogether.

To test lentiviral vector production, enhanced green fluorescent protein (eGFP) was selected as a gene of interest (GOI). It was put under the CMV promoter for a constitutive expression. Bleomycin resistance marker (BleoR) was introduced in the transfer vector to make the selection process more efficient.

In the traditional approach, the integration of an expression cassettes relies on the random integration events. Therefore, it has not been a controlled, efficient process by nature. Furthermore, the final selected clones can be false-positive (i.e., not expressing the intended GOI) as the fragmented, partial antibiotics marker(s) with incomplete expression cassettes can integrate into the chromosome by chance.

To avoid these unwanted events during the producer cell line generation, all the expression cassettes in the packaging and transfer vector plasmids were flanked by PIGGYBAC® inverted terminal repeat (ITR) sequences. PIGGYBAC® transposase specifically recognizes these ITR sequences to promote a site specific recombination in vivo. Therefore, upon the co-transfection of PIGGYBAC® transposase mRNA, the plasmid region that contains the whole expression cassette is efficiently integrated into the chromosome of the cell.

The schematic of the packaging vector is shown in FIG. 1; the schematic of the transfer vector is shown in FIG. 2. The sequence encoding eGFP with its promoter are shown. Also shown are PIGGYBAC® 5' and 3'ITR. The elements for the production of lentiviral vector such as 5' LTR, HIV-1 ψ, RRE, cPPT/CTS, and 3'LTR are also shown.

The nucleic acid sequence for the packaging vector shown in FIG. 1 is provided below:

(SEQ ID NO: 1)

```
ATGAGTATTCAACATTTCCGTGTCGCCCTTATTCCCTTTTTTGCGGCATTTTGCCTTCC

TGTTTTTGCTCACCCAGAAACGCTGGTGAAAGTAAAAGATGCTGAAGATCAGTTGGG

TGCACGAGTGGGTTACATCGAACTGGATCTCAACAGCGGTAAGATCCTTGAGAGTTT

TCGCCCCGAAGAACGTTTTCCAATGATGAGCACTTTTAAAGTTCTGCTATGTGGCGC

GGTATTATCCCGTATTGACGCCGGGCAAGAGCAACTCGGTCGCCGCATACACTATTC

TCAGAATGACTTGGTTGAGTACTCACCAGTCACAGAAAAGCATCTTACGGATGGCAT

GACAGTAAGAGAATTATGCAGTGCTGCCATAACCATGAGTGATAACACTGCGGCCA
```

-continued

```
ACTTACTTCTGACAACGATCGGAGGACCGAAGGAGCTAACCGCTTTTTTGCACAACA

TGGGGGATCATGTAACTCGCCTTGATCGTTGGGAACCGGAGCTGAATGAAGCCATA

CCAAACGACGAGCGTGACACCACGATGCCTGTAGCAATGGCAACAACGTTGCGCAA

ACTATTAACTGGCGAACTACTTACTCTAGCTTCCCGGCAACAATTAATAGACTGGAT

GGAGGCGGATAAAGTTGCAGGACCACTTCTGCGCTCGGCCCTTCCGGCTGGCTGGTT

TATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGG

CAACTATGGATGAACGAAATAGACAGATCGCTGAGATAGGTGCCTCACTGATTAAG

CATTGGTAACTGTCAGACCAAGTTTACTCATATATACTTTAGATTGATTTAAAACTTC

ATTTTTAATTTAAAAGGATCTAGGTGAAGATCCTTTTTGATAATCTCATGACCAAAA

TCCCTTAACGTGAGTTTTCGTTCCACTGAGCGTCAGACCCCGTAGAAAAGATCAAAG

GATCTTCTTGAGATCCTTTTTTTCTGCGCGTAATCTGCTGCTTGCAAACAAAAAAACC

ACCGCTACCAGCGGTGGTTTGTTTGCCGGATCAAGAGCTACCAACTCTTTTTCCGAA

GGTAACTGGCTTCAGCAGAGCGCAGATACCAAATACTGTCCTTCTAGTGTAGCCGTA

GTTAGGCCACCACTTCAAGAACTCTGTAGCACCGCCTACATACCTCGCTCTGCTAAT

CCTGTTACCAGTGGCTGCTGCCAGTGGCGATAAGTCGTGTCTTACCGGGTTGGACTC

AAGACGATAGTTACCGGATAAGGCGCAGCGGTCGGGCTGAACGGGGGGTTCGTGCA

CACAGCCCAGCTTGGAGCGAACGACCTACACCGAACTGAGATACCTACAGCGTGAG

CTATGAGAAAGCGCCACGCTTCCCGAAGGGAGAAAGGCGGACAGGTATCCGGTAAG

CGGCAGGGTCGGAACAGGAGAGCGCACGAGGGAGCTTCCAGGGGGAAACGCCTGG

TATCTTTATAGTCCTGTCGGGTTTCGCCACCTCTGACTTGAGCGTCGATTTTTGTGAT

GCTCGTCAGGGGGGCGGAGCCTATGGAAAAACGCCAGCAACGCGGCCTTTTTACGG

TTCCTGGCCTTTTGCTGGCCTTTTGCTCACATGTTCTTTCCTGCGTTATCCCCTGATTC

TGTGGATAACCGTATTACCGCCTTTGAGTGAGCTGATACCGCTCGCCGCAGCCGAAC

GACCGAGCGCAGCGAGTCAGTGAGCGAGGAAGCGGAAGAGCGCCCAATACGCAAA

CCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTA

GGCACCCCAGGCTTTACACTTTATGCTTCCGGCTCGTATGTTGTGTGGAATTGTGAGC

GGATAACAATTTCACACAGGAAACAGCTATGACCATGATTACGCCAAGCGCGCCCG

CCGGGTAACTCACGGGGTATCCATGTCCATTTCTGCGGCATCCAGCCAGGATACCCG

TCCTCGCTGACGTAATATCCCAGCGCCGCACCGCTGTCATTAATCTGCACACCGGCA

CGGCAGTTCCGGCTGTCGCCGGTATTGTTCGGGTTGCTGATGCGCTTCGGGCTGACC

ATCCGGAACTGTGTCCGGAAAAGCCGCGACGAACTGGTATCCCAGGTGGCCTGAAC

GAACAGTTCACCGTTAAAGGCGTGCATGGCCACACCTTCCCGAATCATCATGGTAAA

CGTGCGTTTTCGCTCAACGTCAATGCAGCAGCAGTCATCCTCGGCAAACTCTTTCCA

TGCCGCTTCAACCTCGCGGGAAAAGGCACGGGCTTCTTCCTCCCCGATGCCCAGATA

GCGCCAGCTTGGGCGATGACTGAGCCGGAAAAAAGACCCGACGATATGATCCTGAT

GCAGCTAGATTAACCCTAGAAAGATAGTCTGCGTAAAATTGACGCATGCATTCTTGA

AATATTGCTCTCTCTTTCTAAATAGCGCGAATCCGTCGCTGTGCATTTAGGACATCTC

AGTCGCCGCTTGGAGCTCCCGTGAGGCGTGCTTGTCAATGCGGTAAGTGTCACTGAT

TTTGAACTATAACGACCGCGTGAGTCAAAATGACGCATGATTATCTTTTACGTGACT
```

-continued

```
TTTAAGATTTAACTCATACGATAATTATATTGTTATTTCATGTTCTACTTACGTGATA
ACTTATTATATATATATTTTCTTGTTATAGATATCAAGCTTATCGATACCGTCGACCT
CGAGGGGGGGCCCGGTACCCAATTCGCCCTATAGTGAGTCGTATTAAGATCTAATTA
ACCCTCACTAAAGGGAACAAAAGCTGGAGCTCCACCGCGGTGGCGGCCGCTCTAGA
GGGACAGCCCCCCCCAAAGCCCCCAGGGATGTAATTACGTCCCTCCCCCGCTAGG
GGGCAGCAGCGAGCCGCCCGGGGCTCCGCTCCGGTCCGGCGCTCCCCCCGCATCCC
CGAGCCGGCAGCGTGCGGGACAGCCCGGGCACGGGGAAGGTGGCACGGGATCGC
TTTCCTCTGAACGCTTCTCGCTGCTCTTTGAGCCTGCAGACACCTGGGGGGATACGG
GGAAAAAGCCATACCAATGGGCCCTAAAAAAGGAATCCAGTCAATTCCGGGGCTAA
ACCTGGCTGCCACTGTTTCTTTAGGGACTTCGTTCCTGTGAGGACAccTGCAggCCGGC
CGGATccTAGgTATacGCGtTAATTAaAGCTTGTTAACGACATTGATTATTGACTAGTTA
TTAATAGTAATCAATTACGGGGTCATTAGTTCATAGCCCATATATGGAGTTCCGCGT
TACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACG
TCAATGGGTGGAGTATTTACGGTAAACTGCCCACTTGGCAGTACATCAAGTGTATCA
TATGCCAAGTACGCCCCCTATTGACGTCAATGACGGTAAATGGCCCGCCTGGCATTA
TGCCCAGTACATGACCTTATGGGACTTTCCTACTTGGCAGTACATCTACGTATTAGTC
ATCGCTATTACCATGGTGATGCGGTTTTGGCAGTACATCAATGGGCGTGGATAGCGG
TTTGACTCACGGGGATTTCCAAGTCTCCACCCCATTGACGTCAATGGGAGTTTGTTTT
GGAACCAAAATCAACGGGACTTTCCAAAATGTCGTAACAACTCCGCCCCATTGACG
CAAATGGGCGGTAGGCGTGTACGGTGGGAGGTCTATATAAGCAGAGCTCTCCCTAT
CAGTGATAGAGATCTCCCTATCAGTGATAGAGATCGTCGACGAGgtgagtttggggacccttgatt
gttctttcttttttcgctattgtaaaattcatgttatatggagggggcaaagttttcagggtgttgtttagaatgggaagatgtcccttgtatcaccatggac
cctcatgataattttgtttctttcactttctactctgttgacaaccattgtctcctcttattttcttttcattttctgtaacttttttcgttaaactttagct
tgcatttgtaacgaattttaaattcacttttgtttatttgtcagattgtaagtactttctctaatcactttttttttcaaggcaatcagggtatattatatt
gtacttcagcacagttttagagaacaattgttataattaaatgataaggtagaatatttctgcatataaattctggctggcgtggaaatattcttattgg
tagaaacaactacatcctggtcatcatcctgcctttctctttatggttacaatgatatacactgtttgagatgaggataaaatactctgagtccaaa
ccgggcccctctgctaaccatgttcatgccttcttcttttttcctacagAGACGCCATCCACGCTGTTTTGACCTCCT
GCCACCATGGCTGGAAGATCTGGCGACTCTGACGAGGACCTGCTGAAAGCTGTGCG
GCTGATCAAGTTCCTGTACCAGAGCAACCCTCCACCTAATCCTGAGGGCACCAGACA
GGCCAGAAGAAACAGGCGGAGAAGATGGCGCGAGCGGCAGAGACAGATCCACTCC
ATCTCCGAGCGGATCCTGTCCACCTACCTGGGAAGATCCGCTGAGCCTGTTCCTCTG
CAGCTGCCTCCTCTGGAAAGACTGACCCTGGACTGCAACGAGGACTGCGGCACCTCT
GGAACACAAGGCGTTGGCTCTCCACAGATCCTGGTGGAAAGCCCCACCATCCTGGA
ATCCGGCGCCAAAGAATGAGTTTAAACCGCTGATCAGCCTCGACTGTGCCTTCTAGT
TGCCAGCCATCTGTTGTTTGCCCCTCCCCCGTGCCTTCCTTGACCCTGGAAGGTGCCA
CTCCCACTGTCCTTTCCTAATAAAATGAGGAAATTGCATCGCATTGTCTGAGTAGGT
GTCATTCTATTCTGGGGGGTGGGGTGGGGCAGGACAGCAAGGGGGAGGATTGGGAA
GACAATAGCAGGCATGCTGGGGATGCGGTGGGCTCTATGGTACCACAGATTCCCGC
TTCTCGACTAATTCCTCTTGTACGTGTACTTCGACATGTACCTCCCGTGGCACTTGTT
```

-continued

```
GGTGGTGAAGTTCACGTGTAGGCTCCCGCTTCCGTTCGGGATGCTCCCGTGGGTCTG

GTACTCTTAGTTCCACCAGCTCCCGCCGGGAGAGGGGAAGCGGAAGCTGTAGGACC

GATGGTCGAAGTAGACATTGATTATTGACTAGTTATTAATAGTAATCAATTACGGGG

TCATTAGTTCATAGCCCATATATGGAGTTCCGCGTTACATAACTTACGGTAAATGGC

CCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGG

TAAACTGCCCACTTGGCAGTACATCAAGTGTATCATATGCCAAGTACGCCCCCTATT

GACGTCAATGACGGTAAATGGCCCGCCTGGCATTATGCCCAGTACATGACCTTATGG

GACTTTCCTACTTGGCAGTACATCTACGTATTAGTCATCGCTATTACCATGGTGATGC

GGTTTTGGCAGTACATCAATGGGCGTGGATAGCGGTTTGACTCACGGGGATTTCCAA

GTCTCCACCCCATTGACGTCAATGGGAGTTTGTTTTGGAACCAAAATCAACGGGACT

TTCCAAAATGTCGTAACAACTCCGCCCCATTGACGCAAATGGGCGGTAGGCGTGTAC

GGTGGGAGGTCTATATAAGCAGAGCTCTCCCTATCAGTGATAGAGATCTCCCTATCA

GTGATAGAGATCGTCGACGAGGTAAGTATCAAGGTTACAAGACAGGTTTAAGGAGA

CCAATAGAAACTGGGCTTGTCGAGACAGAGAAGACTCTTGCGTTTCTGATAGGCACC

TATTGGTCTTACTGACATCCACTTTGCCTTTCTCTCCACAGGCGGCCGCGACACTGCC

ACCATGAAGTGCCTGCTGTACCTGGCCTTTCTGTTCATCGGCGTGAACTGTAAGTTTA

CCATCGTGTTCCCTCACAATCAGAAGGGCAACTGGAAGAATGTGCCAAGCAACTAC

CACTATTGCCCCAGCTCCTCTGACCTGAACTGGCACAATGATCTGATCGGCACAGCC

CTGCAGGTGAAGATGCCAAAGAGCCACAAGGCCATCCAGGCAGACGGATGGATGTG

CCACGCCTCCAAGTGGGTGACCACATGTGATTTTCGGTGGTACGGCCCAAAGTATAT

CACCCACAGCATCAGATCCTTCACACCCTCTGTGGAGCAGTGCAAGGAGAGCATCG

AGCAGACAAAGCAGGGCACCTGGCTGAATCCTGGCTTTCCCCCTCAGTCCTGTGGAT

ACGCAACAGTGACCGACGCAGAGGCCGTGATCGTGCAGGTGACCCCACACCACGTG

CTGGTGGACGAGTATACAGGCGAGTGGGTGGATTCCCAGTTCATCAACGGCAAGTG

CTCTAATTACATCTGTCCCACCGTGCACAACTCCACCACATGGCACTCTGATTATAA

GGTGAAGGGCCTGTGCGATTCTAATCTGATCAGCATGGACATCACATTCTTTTCTGA

GGATGGAGAGCTGAGCTCCCTGGGCAAGGAGGGAACCGGCTTTCGGAGCAACTACT

TCGCCTATGAGACAGGCGGCAAGGCCTGCAAGATGCAGTACTGTAAGCACTGGGGC

GTGAGGCTGCCAAGCGGCGTGTGGTTCGAGATGGCCGACAAGGATCTGTTTGCTGCC

GCCAGGTTCCCAGAGTGCCCAGAGGGATCTAGCATCTCTGCCCCAAGCCAGACCTCC

GTGGACGTGTCCCTGATCCAGGATGTGGAGCGGATCCTGGACTACTCCCTGTGCCAG

GAGACATGGTCTAAGATCAGAGCCGGCCTGCCTATCAGCCCAGTGGACCTGTCCTAT

CTGGCACCAAAGAACCCTGGAACAGGACCAGCCTTTACCATCATCAATGGCACACT

GAAGTACTTCGAGACCCGGTATATCAGAGTGGACATCGCCGCCCCTATCCTGAGCA

GGATGGTGGGCATGATCTCCGGAACCACAACCGAGAGGGAGCTGTGGGACGATTGG

GCACCTTACGAGGATGTGGAGATCGGCCCAAATGGCGTGCTGCGGACCTCCTCTGG

CTACAAGTTTCCCCTGTATATGATCGGCCACGGCATGCTGGACAGCGATCTGCACCT

GAGCTCCAAGGCCCAGGTGTTCGAGCACCCACACATCCAGGACGCAGCATCTCAGC

TGCCTGACGATGAGAGCCTGTTCTTTGGCGATACCGGCCTGTCCAAGAACCCTATCG

AGCTGGTGGAGGGCTGGTTTTCTAGCTGGAAGTCCTCTATCGCCTCTTTCTTTTTCAT
```

-continued

```
CATCGGCCTGATCATCGGCCTGTTCCTGGTGCTGAGAGTGGGCATCCACCTGTGCAT

CAAGCTGAAGCACACCAAGAAGAGGCAGATCTATACAGACATCGAGATGAATCGCC

TGGGCAAGTGATCTAGACTCGAGCGGCCGCCACTGTGCTGGATATCTGCAGAATTCC

ACCACACTGGACTAGTGGATCCGAGCTCGGTACCAAGCTTAAGTTTAAACCGCTGAT

CAGCCTCGACTGTGCCTTCTAGTTGCCAGCCATCTGTTGTTTGCCCCTCCCCCGTGCC

TTCCTTGACCCTGGAAGGTGCCACTCCCACTGTCCTTTCCTAATAAAATGAGGAAAT

TGCATCGCATTGTCTGAGTAGGTGTCATTCTATTCTGGGGGTGGGGGGGCAGGA

CAGCAAGGGGGAGGATTGGGAAGACAATAGCAGGCATGCTGGGGATGCGGTGGGC

TCTATGGCATGCCGTCGTCTTGGAAGTAGTTGGTGTGGGTCCCGTAGGGGCTGAAGA

AATTCGTCAGGAAGGGACTCCCGAAGTGTACCCTCTCTCAGTGGTGTATGCTTCTGC

CCCCGCACGACTGGCGATGGGTCCTGTGGTCGGAGGTCCTGCCGACGGAGTAGATG

TTGCAGTTCTAGTCTCCCCACTTGAAGGGTAGGTTGCGACATTGATTATTGACTAGTT

ATTAATAGTAATCAATTACGGGGTCATTAGTTCATAGCCCATATATGGAGTTCCGCG

TTACATAACTTACGGTAAATGGCCCGCCTGGCTGACCGCCCAACGACCCCCGCCCAT

TGACGTCAATAATGACGTATGTTCCCATAGTAACGCCAATAGGGACTTTCCATTGAC

GTCAATGGGTGGAGTATTTACGGTAAACTGCCCACTTGGCAGTACATCAAGTGTATC

ATATGCCAAGTACGCCCCCTATTGACGTCAATGACGGTAAATGGCCCGCCTGGCATT

ATGCCCAGTACATGACCTTATGGGACTTTCCTACTTGGCAGTACATCTACGTATTAGT

CATCGCTATTACCATGGTGATGCGGTTTTGGCAGTACATCAATGGGCGTGGATAGCG

GTTTGACTCACGGGGATTTCCAAGTCTCCACCCCATTGACGTCAATGGGAGTTTGTTT

TGGAACCAAAATCAACGGGACTTTCCAAAATGTCGTAACAACTCCGCCCCATTGAC

GCAAATGGGCGGTAGGCGTGTACGGTGGGAGGTCTATATAAGCAGAGCTCTCCCTA

TCAGTGATAGAGATCTCCCTATCAGTGATAGAGATCGTCGACGAGGTAAGTATCAA

GGTTACAAGACAGGTTTAAGGAGACCAATAGAAACTGGGCTTGTCGAGACAGAGAA

GACTCTTGCGTTTCTGATAGGCACCTATTGGTCTTACTGACATCCACTTTGCCTTTCT

CTCCACAGGTGTCCACTCCCAGTTCAATTACAGCTCTTAAGGCTAGAGTACTTAATA

CGACTCACTATAGGCTAGCCTCGAGAATTCACGCGCACGGCAAGAGGCGAGGGGCG

GCGACTGGTGAGTACGCCAGGATCCGCGGATCCATGGGCGCCCGCGCCAGCGTGCT

GTCCGGCGGCGAGCTGGATAAATGGGAAAAAATTCGGTTAAGGCCAGGGGGAAAG

AAACAATATAAACTAAAACATATAGTATGGGCAAGCAGGGAGCTAGAACGATTCGC

AGTTAATCCTGGCCTTTTAGAGACATCAGAAGGCTGTAGACAAATACTGGGACAGCT

ACAACCATCCCTTCAGACAGGATCAGAAGAACTTAGATCATTATATAATACAATAGC

AGTCCTCTATTGTGTGCATCAAAGGATAGATGTAAAAGACACCAAGGAAGCCTTAG

ATAAGATAGAGGAAGAGCAAAACAAAAGTAAGAAAAAGGCACAGCAAGCAGCAGC

TGACACAGGAAACAACAGCCAGGTCAGCCAAAATTACCCTATAGTGCAGAACCTCC

AGGGGCAAATGGTACATCAGGCCATATCACCTAGAACTTTAAATGCATGGGTAAAA

GTAGTAGAAGAGAAGGCTTTCAGCCCAGAAGTAATACCCATGTTTTCAGCATTATCA

GAAGGAGCCACCCCACAAGATTTAAATACCATGCTAAACACAGTGGGGGACATCA

AGCAGCCATGCAAATGTTAAAAGAGACCATCAATGAGGAAGCTGCAGAATGGGATA

GATTGCATCCAGTGCATGCAGGGCCTATTGCACCAGGCCAGATGAGAGAACCAAGG
```

```
GGAAGTGACATAGCAGGAACTACTAGTACCCTTCAGGAACAAATAGGATGGATGAC

ACATAATCCACCTATCCCAGTAGGAGAAATCTATAAAAGATGGATAATCCTGGGATT

AAATAAAATAGTAAGAATGTATAGCCCTACCAGCATTCTGGACATAAGACAAGGAC

CAAAGGAACCCTTTAGAGACTATGTAGACCGATTCTATAAAACTCTAAGAGCCGAG

CAAGCTTCACAAGAGGTAAAAAATTGGATGACAGAAACCTTGTTGGTCCAAAATGC

GAACCCAGATTGTAAGACTATTTTAAAAGCATTGGGACCAGGAGCGACACTAGAAG

AAATGATGACAGCATGTCAGGGAGTGGGGGGACCCGGCCATAAAGCAAGAGTTTTG

GCTGAAGCAATGAGCCAAGTAACAAATCCAGCTACCATAATGATACAGAAAGGCAA

TTTTAGGAACCAAAGAAAGACTGTTAAGTGTTTCAATTGTGGCAAAGAAGGGCACA

TAGCCAAAAATTGCAGGGCCCCTAGGAAAAAGGGCTGTTGGAAATGTGGAAAGGAA

GGACACCAAATGAAAGATTGTACTGAGAGACAGGCTAATTTTTTAGGGAAGATCTG

GCCTTCCCACAAGGGAAGGCCAGGGAATTTTCTTCAGAGCAGACCAGAGCCAACAG

CCCCACCAGAAGAGAGCTTCAGGTTTGGGGAAGAGACAACAACTCCCTCTCAGAAG

CAGGAGCCGATAGACAAGGAACTGTATCCTTTAGCTTCCCTCAGATCACTCTTTGGC

AGCGACCCCTCGTCACAATAAAGATAGGGGGGCAATTAAAGGAAGCTCTATTAGAT

ACAGGAGCAGATGATACAGTATTAGAAGAAATGAATTTGCCAGGAAGATGGAAACC

AAAAATGATAGGGGGAATTGGAGGTTTTATCAAAGTAaGACAGTATGATCAGATACT

CATAGAAATCTGCGGACATAAAGCTATAGGTACAGTATTAGTAGGACCTACACCTGT

CAACATAATTGGAAGAAATCTGTTGACTCAGATTGGCTGCACTTTAAATTTTCCCAT

TAGTCCTATTGAGACTGTACCAGTAAAATTAAAGCCAGGAATGGATGGCCCAAAAG

TTAAACAATGGCCATTGACAGAAGAAAAAATAAAAGCATTAGTAGAAATTTGTACA

GAAATGGAAAAGGAAGGAAAAATTTCAAAAATTGGGCCTGAAAATCCATACAATAC

TCCAGTATTTGCCATAAAGAAAAAAGACAGTACTAAATGGAGAAAATTAGTAGATT

TCAGAGAACTTAATAAGAGAACTCAAGATTTCTGGGAAGTTCAATTAGGAATACCA

CATCCTGCAGGGTTAAAACAGAAAAAATCAGTAACAGTACTGGATGTGGGCGATGC

ATATTTTTCAGTTCCCTTAGATAAAGACTTCAGGAAGTATACTGCATTTACCATACCT

AGTATAAACAATGAGACACCAGGGATTAGATATCAGTACAATGTGCTTCCACAGGG

ATGGAAAGGATCACCAGCAATATTCCAGTGTAGCATGACAAAAATCTTAGAGCCTTT

TAGAAAACAAAATCCAGACATAGTCATCTATCAATACATGGATGATTTGTATGTAGG

ATCTGACTTAGAAATAGGGCAGCATAGAACAAAAATAGAGGAACTGAGACAACATC

TGTTGAGGTGGGGATTTACCACACCAGACAAAAAACATCAGAAAGAACCTCCATTC

CTTTGGATGGGTTATGAACTCCATCCTGATAAATGGACAGTACAGCCTATAGTGCTG

CCAGAAAAGGACAGCTGGACTGTCAATGACATACAGAAATTAGTGGGAAAATTGAA

TTGGGCAAGTCAGATTTATGCAGGGATTAAAGTAAGGCAATTATGTAAACTTCTTAG

GGGAACCAAAGCACTAACAGAAGTAGTACCACTAACAGAAGAAGCAGAGCTAGAA

CTGGCAGAAAACAGGGAGATTCTAAAAGAACCGGTACATGGAGTGTATTATGACCC

ATCAAAAGACTTAATAGCAGAAATACAGAAGCAGGGGCAAGGCCAATGGACATATC

AAATTTATCAAGAGCCATTTAAAAATCTGAAAACAGGAAAgTATGCAAGAATGAAG

GGTGCCCACACTAATGATGTGAAACAATTAACAGAGGCAGTACAAAAAATAGCCAC

AGAAAGCATAGTAATATGGGGAAAGACTCCTAAATTTAAATTACCCATACAAAAGG

AAACATGGGAAGCATGGTGGACAGAGTATTGGCAAGCCACCTGGATTCCTGAGTGG
```

-continued

```
GAGTTTGTCAATACCCCTCCCTTAGTGAAGTTATGGTACCAGTTAGAGAAAGAACCC

ATAATAGGAGCAGAAACTTTCTATGTAGATGGGGCAGCCAATAGGGAAACTAAATT

AGGAAAAGCAGGATATGTAACTGACAGAGGAAGACAAAAAGTTGTCCCCCTAACGG

ACACAACAAATCAGAAGACTGAGTTACAAGCAATTCATCTAGCTTTGCAGGATTCG

GGATTAGAAGTAAACATAGTGACAGACTCACAATATGCATTGGGAATCATTCAAGC

ACAACCAGATAAGAGTGAATCAGAGTTAGTCAGTCAAATAATAGAGCAGTTAATAA

AAAAGGAAAAAGTCTACCTGGCATGGGTACCAGCACACAAAGGAATTGGAGGAAA

TGAACAAGTAGATAAATTGGTCAGTGCTGGAATCAGGAAAGTACTATTTTTAGATGG

AATAGATAAGGCCCAAGAAGAACATGAGAAATATCACAGTAATTGGAGAGCAATG

GCTAGTGATTTTAACCTACCACCTGTAGTAGCAAAAGAAATAGTAGCCAGCTGTGAT

AAATGTCAGCTAAAAGGGGAAGCCATGCATGGACAAGTAGACTGTAGCCCAGGAAT

ATGGCAGCTAGATTGTACACATTTAGAAGGAAAAGTTATCTTGGTAGCAGTTCATGT

AGCCAGTGGATATATAGAAGCAGAAGTAATTCCAGCAGAGACAGGGCAAGAAACA

GCATACTTCCTCTTAAAATTAGCAGGAAGATGGCCAGTAAAAACAGTACATACAGA

CAATGGCAGCAATTTCACCAGTACTACAGTTAAGGCCGCCTGTTGGTGGGCGGGAT

CAAGCAGGAATTTGGCATTCCCTACAATCCCCAAAGTCAAGGAGTAATAGAATCTAT

GAATAAAGAATTAAAGAAAATTATAGGACAGGTAAGAGATCAGGCTGAACATCTTA

AGACAGCAGTACAAATGGCAGTATTCATCCACAATTTTAAAAGAAAAGGGGGGATT

GGGGGGTACAGTGCAGGGGAAAGAATAGTAGACATAATAGCAACAGACATACAAA

CTAAAGAATTACAAAAACAAATTACAAAAATTCAAAATTTTCGGGTTTATTACAGGG

ACAGCAGAGATCCAGTTTGGAAAGGACCAGCAAAGCTCCTCTGGAAAGGTGAAGGG

GCAGTAGTAATACAAGATAATAGTGACATAAAAGTAGTGCCAAGAAGAAAAGCAA

AGATCATCAGGGATTATGGAAAACAGATGGCAGGTGATGATTGTGTGGCAAGTAGA

CAGGATGAGGATTAACACCCATAGAATGGCCAAGGCAAAGAGAAGAGTGGTGCAG

AGAGAAAAAGAGCAGTGGGAATAGGAGCTTTGTTCCTTGGGTTCTTGGGAGCAGC

AGGAAGCACTATGGGCGCAGCGTCAATGACGCTGACGGTACAGGCCAGACAATTAT

TGTCTGATATAGTGCAGCAGCAGAACAATTTGCTGAGGGCTATTGAGGCGCAACAG

CATCTGTTGCAACTCACAGTCTGGGGCATCAAACAGCTCCAGGCAAGAATCCTGGCT

GTGGAAAGATACCTAAAGGATCAACAGCTCCTGGGGATTTGGGGTTGCTCTGGAAA

ACTCATTTGCACCACTGCTGTGCCGCGGCCGCAAAAAAGGGGCTCGTCCCTGTTTCC

GGAGGAATTTGCAAGCGGGGTCTTGCATGACGGGGAGGCAAACCCCCGTTCGGCCG

CAGTCCGGCCGGCCCGAGACTCGAACCGGGGGTCCTGCGACTCAACCCTTGGAAAA

TAACCCTCCGGCTACAGGGAGCGAGCCACTTAATGCTTTCGCTTTCCAGCCTAACCG

CTTACGCCGCGCGCGgCCAGTGGCCAAAAAAGCTAGCGCAGCAGCCGCCGCGCCTG

GAAGGAAGCCAAAAGGAGCGCTCCCCCGTTGTCTGACGTCGCACACCTGGGTTCGA

CACGCGGGCGGTAACCGCATGGATCACGGCGGACGGCCGGATCCGGGGTTCGAACC

CCGGTCGTCCGCCATGATACCCTTGCGAATTTATCCACCAGACCACGGAAGAGTGCC

CGCGGCCGCTTCGAGCAGACATGATAAGATACATTGATGAGTTTGGACAAACCACA

ACTAGAATGCAGTGAAAAAAATGCTTTATTTGTGAAATTTGTGATGCTATTGCTTTA

TTTGTAACCATTATAAGCTGCAATAAACAAGTTCGGGACACTACGTCTTCTTTTGTG
```

-continued

```
AGCCGACCCTCCGGTTGTGGCTCTACGACATGGGCGACTGCCGCCGGACCTTCCGT

CTTCGCTGTACCGGACTTCGAGCACCCGCCCCCGGTGGACTAGACGTTGAAGTTCT

GGTGTATGTCTAGGTTCTTTGGGCGATTCTTGGAGTTCTACGGGCCGCAGATGATAC

ACCTGggggttgggggttgcgccttttccaaggcagccctgggtttgcgcagggacgcggctgctctgggcgtggttccgggaaacgc agcggcgccgaccctgggtctcgcacattcttcacgtccgttcgcagcgtcacccggatcttcgccgctaccccttgtgggcccccggcga cgcttcctgctccgccccctaagtcgggaaggttccttgcggttcgcggcgtgccggacgtgacaaacggaagccgcacgtctcactagtac cctcgcagacggacagcgccagggagcaatggcagcgcgccgaccgcgatgggctgtggccaatagcggctgctcagcagggcgcg ccgagagcagcggccgggaaggggcggtgcgggaggcgggtgtggggcggtagtgtgggccctgttcctgcccgcgcggtgttccg cattctgcaagcctccggagcgcacgtcggcagtcggctccctcgttgaccgaatcaccgacctctctcccccaggggggatctGTAAG

TATCAAGGTTACAAGACAGGTTTAAGGAGACCAATAGAAACTGGGCTTGTCGAGAC

AGAGAAGACTCTTGCGTTTCTGATAGGCACCTATTGGTCTTACTGACATCCACTTTGC

CTTTCTCTCCACAGctcctgggcaacgtgctggttattgtgctgtctcatcattttggcaaagaattgtaatacgactcactatagg gcgaGCCACCatggctagattagataaaagtaaagtgattaacagcgcattagagctgcttaatgaggtcggaatcgaaggtttaacaa cccgtaaactcgcccagaagctaggtgtagagcagcctacattgtattggcatgtaaaaaataagcgggctttgctcgacgccttagccattg agatgttagataggcaccatactcacttttgcccttttagaagggggaaaagctggcaagattttttacgtaataacgctaaaagttttagatgtgctttt actaagtcatcgcgatggagcaaaagtacatttaggtacacggcctacagaaaaacagtatgaaactctcgaaaatcaattagcctttttatgc caacaaggttttttcactagagaatgcCttatatgcactcagcgcCgtggggcattttactttaggttgcgtattggaagatcaagagcatcaag tcgctaaagaagaaagggaaacacctactactgatagtatgccgccattattacgacaagctatcgaattatttgatcaccaaggtgcagagc cagccttcttattcggccttgaattgatcatatgcggattagaaaaacaacttaaatgtgaaagtgggtccccaaaaaagaagagaaaggtcg acggcggtggtgctttgtctcctcagcactctgctgtcactcaaggaagtatcatcaagaacaaggagggcatggatgctaagtcactaact gcctggtcccggacactggtgaccttcaaggatgtatttgtggacttcaccagggaggagtggaagctgctggacactgctcagcagatcg tgtacagaaatgtgatgctggagaactataagaacctggtttccttgggttatcagcttactaagccagatgtgatcctccggttggagaaggg agaagagccctggctggtggagagagaaattccaccaagagacccatcctgattcagagactgcatttgaaatcaaatcatcagtttaagcgt acagcggctcccgggagttctagggatctgcccctctccctcccccccccctaacgttactggccgaagccgcttggaataaggccggtgt gcgtttgtctatatgttatttttccaccatattgccgtcttttggcaatgtgagggcccgaaacctggccctgtcttcttgacgagcattcctaggg gtctttcccctctcgccaaaggaatgcaaggtctgttgaatgtcgtgaaggaagcagttcctctggaagcttcttgaagacaaacaacgtctgt agcgacccttttgcaggcagcggaaccccccacctggcgacaggtgcctctgcggccaaaagccacgtgtataagatacacctgcaaagg cggcacaaccccagtgccacgttgtgagttggatagttgtggaaagagtcaaatggctctcctcaagcgtattcaacaaggggctgaagga tgcccagaaggtacccccattgtatgggatctgatctggggcctcggtgcacatgctttacatgtgtttagtcgaggttaaaaaaacgtctaggc cccccgaaccacggggacgtggttttcctttgaaaaacacgatgataaggatccaccggagGCCACCatgaccgagtacaagccca cggtgcgcctcgccacccgcgacgacgtcccccagggccgtacgcaccctcgccgccgcgttcgccgactaccccgccacgcgccaca ccgtcgatccggaccgccacatcgagcgggtcaccgagctgcaagaactcttcctcacgcgcgtcgggctcgacatcggcaaggtgtgg gtcgcggacgacggcgccgcggtggcggtctggaccacgccggagagcgtcgaagcgggggcggtgttcgccgagatcggcccgcg catggccgagttgagcggttcccggctggccgcgcagcaacagatggaaggcctcctggcgccgcaccggcccaaggagcccgcgtg gttcctggccaccgtcggcgtctcgcccgaccaccagggcaagggtctgggcagcgccgtcgtgctcccccggagtggaggcggccgag cgcgccggggtgcccgccttcctggagacctccgcgccccgcaacctcccctctacgagcggctcggcttccacgtcaccgccgacgtc gaggtgcccgaaggaccgcgcacctggtgcatgacccgcaagcccggtgcctgaCCGCGTCTGGAACatgcatCGGTA

CCTTTAAGACCAATGACTTACAAGGCAGCTGTAGATCTTAGCCACTTTTTAAAAGAA

AAGGGGGGACGTAGTAGTTCATGTCATCTTATTATTCAGTATTTATAACTTGCAAAG

AAATGAATATCAGAGAGTGAGAGGAACTTGTTTATTGCAGCTTATAATGGTTACAAA

TAAAGCAATAGCATCACAAATTTCACAAATAAAGCATTTTTTTCACTGCATTCTAGT
```

-continued

```
TGTGGTTTGTCCAAACTCATCAATGTATCTTAGTTAACGAATTCGGCGCGCcAATtgAT

CaGCGctTAAgCTAgcGATCgcGGGACTTTCCACACCCTAACTGACACACATTCCACAGA

ATTCCCATCACAAAGCTCTGACCTCAATCCTATAGAAAGGAGGAATGAGCCAAAAT

TCACCCAACTTATTGTGGGAAGCTGGCCTTGGAGGCCTTTTCCCCGTATCCCCCAG

GTGTCTGCAGGCTCAAAGAGCAGCGAGAAGCGTTCAGAGGAAAGCGATCCCGTGCC

ACCTTCCCCGTGCCCGGGCTGTCCCCGCACGCTGCCGGCTCGGGGATGCGGGGGA

GCGCCGGACCGGAGCGGAGCCCCGGGCGGCTCGCTGCTGCCCCCTAGCGGGGAGG

GACGTAATTACATCCCTGGGGGCTTTGGGGGGGGGCTGTCCCTCTAGAACTAGTGGA

TCCCCCGGGCTGCAGGAATTCGATAAAAGTTTTGTTACTTTATAGAAGAAATTTTGA

GTTTTTGTTTTTTTTAATAAATAAATAAACATAAATAAATTGTTTGTTGAATTTATT

ATTAGTATGTAAGTGTAAATATAATAAAACTTAATATCTATTCAAATTAATAAATAA

ACCTCGATATACAGACCGATAAAACACATGCGTCAATTTTACGCATGATTATCTTTA

ACGTACGTCACAATATGATTATCTTTCTAGGGTTAATCTAGCTGCGTGTTCTGCAGCG

TGTCGAGCATCTTCATCTGCTCCATCACGCTGTAAAACACATTTGCACCGCGAGTCT

GCCCGTCCTCCACGGGTTCAAAAACGTGAATGAACGAGGCGCGCTCACTGGCCGTC

GTTTTACAACGTCGTGACTGGGAAAACCCTGGCGTTACCCAACTTAATCGCCTTGCA

GCACATCCCCCTTTCGCCAGCTGGCGTAATAGCGAAGAGGCCCGCACCGATCGCCCT

TCCCAACAGTTGCGCAGCCTGAATGGCGAATGGGACGCGCCCTGTAGCGGCGCATT

AAGCGCGGCGGGTGTGGTGGTTACGCGCAGCGTGACCGCTACACTTGCCAGCGCCC

TAGCGCCCGCTCCTTTCGCTTTCTTCCCTTCCTTTCTCGCCACGTTCGCCGGCTTTCCC

CGTCAAGCTCTAAATCGGGGGCTCCCTTTAGGGTTCCGATTTAGTGCTTTACGGCAC

CTCGACCCCAAAAAACTTGATTAGGGTGATGGTTCACGTAGTGGGCCATCGCCCTGA

TAGACGGTTTTTCGCCCTTTGACGTTGGAGTCCACGTTCTTTAATAGTGGACTCTTGT

TCCAAACTGGAACAACACTCAACCCTATCTCGGTCTATTCTTTTGATTTATAAGGGAT

TTTGCCGATTTCGGCCTATTGGTTAAAAAATGAGCTGATTTAACAAAAATTTAACGC

GAATTTTAACAAAATATTAACGCTTACAATTTAGGTGGCACTTTTCGGGGAAATGTG

CGCGGAACCCCTATTTGTTTATTTTTCTAAATACATTCAAATATGTATCCGCTCATGA

GACAATAACCCTGATAAATGCTTCAATAATATTGAAAAAGGAAGAGT
```

The nucleic acid sequence for the transfer vector shown in FIG. 2 is provided below:

```
                                              (SEQ ID NO: 2)
ATGAGTATTCAACATTTCCGTGTCGCCCTTATTCCCTTTTTTGCGGCATTTTGCCTTCCTGTT

TTTGCTCACCCAGAAACGCTGGTGAAAGTAAAAGATGCTGAAGATCAGTTGGG

TGCACGAGTGGGTTACATCGAACTGGATCTCAACAGCGGTAAGATCCTTGAGAGTTT

TCGCCCCGAAGAACGTTTTCCAATGATGAGCACTTTTAAAGTTCTGCTATGTGGCGC

GGTATTATCCCGTATTGACGCCGGGCAAGAGCAACTCGGTCGCCGCATACACTATTC

TCAGAATGACTTGGTTGAGTACTCACCAGTCACAGAAAAGCATCTTACGGATGGCAT

GACAGTAAGAGAATTATGCAGTGCTGCCATAACCATGAGTGATAACACTGCGGCCA

ACTTACTTCTGACAACGATCGGAGGACCGAAGGAGCTAACCGCTTTTTTGCACAACA

TGGGGGATCATGTAACTCGCCTTGATCGTTGGGAACCGGAGCTGAATGAAGCCATA
```

-continued

```
CCAAACGACGAGCGTGACACCACGATGCCTGTAGCAATGGCAACAACGTTGCGCAA

ACTATTAACTGGCGAACTACTTACTCTAGCTTCCCGGCAACAATTAATAGACTGGAT

GGAGGCGGATAAAGTTGCAGGACCACTTCTGCGCTCGGCCCTTCCGGCTGGCTGGTT

TATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGG

CAACTATGGATGAACGAAATAGACAGATCGCTGAGATAGGTGCCTCACTGATTAAG

CATTGGTAACTGTCAGACCAAGTTTACTCATATATACTTTAGATTGATTTAAAACTTC

ATTTTTAATTTAAAAGGATCTAGGTGAAGATCCTTTTTGATAATCTCATGACCAAAA

TCCCTTAACGTGAGTTTTCGTTCCACTGAGCGTCAGACCCCGTAGAAAAGATCAAAG

GATCTTCTTGAGATCCTTTTTTTCTGCGCGTAATCTGCTGCTTGCAAACAAAAAAACC

ACCGCTACCAGCGGTGGTTTGTTTGCCGGATCAAGAGCTACCAACTCTTTTTCCGAA

GGTAACTGGCTTCAGCAGAGCGCAGATACCAAATACTGTCCTTCTAGTGTAGCCGTA

GTTAGGCCACCACTTCAAGAACTCTGTAGCACCGCCTACATACCTCGCTCTGCTAAT

CCTGTTACCAGTGGCTGCTGCCAGTGGCGATAAGTCGTGTCTTACCGGGTTGGACTC

AAGACGATAGTTACCGGATAAGGCGCAGCGGTCGGGCTGAACGGGGGGTTCGTGCA

CACAGCCCAGCTTGGAGCGAACGACCTACACCGAACTGAGATACCTACAGCGTGAG

CTATGAGAAAGCGCCACGCTTCCCGAAGGGAGAAAGGCGGACAGGTATCCGGTAAG

CGGCAGGGTCGGAACAGGAGAGCGCACGAGGGAGCTTCCAGGGGGAAACGCCTGG

TATCTTTATAGTCCTGTCGGGTTTCGCCACCTCTGACTTGAGCGTCGATTTTTGTGAT

GCTCGTCAGGGGGGCGGAGCCTATGGAAAAACGCCAGCAACGCGGCCTTTTTACGG

TTCCTGGCCTTTTGCTGGCCTTTTGCTCACATGTTCTTTCCTGCGTTATCCCCTGATTC

TGTGGATAACCGTATTACCGCCTTTGAGTGAGCTGATACCGCTCGCCGCAGCCGAAC

GACCGAGCGCAGCGAGTCAGTGAGCGAGGAAGCGGAAGAGCGCCCAATACGCAAA

CCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTA

GGCACCCCAGGCTTTACACTTTATGCTTCCGGCTCGTATGTTGTGTGGAATTGTGAGC

GGATAACAATTTCACACAGGAAACAGCTATGACCATGATTACGCCAAGCGCGCCCG

CCGGGTAACTCACGGGGTATCCATGTCCATTTCTGCGGCATCCAGCCAGGATACCCG

TCCTCGCTGACGTAATATCCCAGCGCCGCACCGCTGTCATTAATCTGCACACCGGCA

CGGCAGTTCCGGCTGTCGCCGGTATTGTTCGGGTTGCTGATGCGCTTCGGGCTGACC

ATCCGGAACTGTGTCCGGAAAAGCCGCGACGAACTGGTATCCCAGGTGGCCTGAAC

GAACAGTTCACCGTTAAAGGCGTGCATGGCCACACCTTCCCGAATCATCATGGTAAA

CGTGCGTTTTCGCTCAACGTCAATGCAGCAGCAGTCATCCTCGGCAAACTCTTTCCA

TGCCGCTTCAACCTCGCGGGAAAAGGCACGGGCTTCTTCCTCCCCGATGCCCAGATA

GCGCCAGCTTGGGCGATGACTGAGCCGGAAAAAAGACCCGACGATATGATCCTGAT

GCAGCTAGATTAACCCTAGAAAGATAGTCTGCGTAAAATTGACGCATGCATTCTTGA

AATATTGCTCTCTCTTTCTAAATAGCGCGAATCCGTCGCTGTGCATTTAGGACATCTC

AGTCGCCGCTTGGAGCTCCCGTGAGGCGTGCTTGTCAATGCGGTAAGTGTCACTGAT

TTTGAACTATAACGACCGCGTGAGTCAAAATGACGCATGATTATCTTTTACGTGACT

TTTAAGATTTAACTCATACGATAATTATATTGTTATTTCATGTTCTACTTACGTGATA
```

-continued

```
ACTTATTATATATATATTTTCTTGTTATAGATATCAAGCTTATCGATACCGTCGACCT
CGAGGGGGGCCCGGTACCCAATTCGCCCTATAGTGAGTCGTATTAAGATCTAATTA
ACCCTCACTAAAGGGAACAAAAGCTGGAGCTCCACCGCGGTGGCGGCCGCTCTAGA
GGGACAGCCCCCCCCAAAGCCCCCAGGGATGTAATTACGTCCCTCCCCCGCTAGG
GGGCAGCAGCGAGCCGCCCGGGGCTCCGCTCCGGTCCGGCGCTCCCCCCGCATCCC
CGAGCCGGCAGCGTGCGGGGACAGCCCGGGCACGGGGAAGGTGGCACGGGATCGC
TTTCCTCTGAACGCTTCTCGCTGCTCTTTGAGCCTGCAGACACCTGGGGGATACGG
GGAAAAAGCCATACCAATGGGCCCTAAAAAAGGAATCCAGTCAATTCCGGGGCTAA
ACCTGGCTGCCACTGTTTCTTTAGGGACTTCGTTCCTGTGAGGACAccTGCAggCCGGC
CGGATccTAGgTATacGCGtTAATTAaAGCTTGTTAACGACATTGATTATTGACTAGTTATTA
ATAGTAATCAATTACGGGGTCATTAGTTCATAGCCCATATATGGAGTTCCGCGT
TACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACG
TCAATGGGTGGAGTATTTACGGTAAACTGCCCACTTGGCAGTACATCAAGTGTATCA
TATGCCAAGTACGCCCCCTATTGACGTCAATGACGGTAAATGGCCCGCCTGGCATTA
TGCCCAGTACATGACCTTATGGGACTTTCCTACTTGGCAGTACATCTACGTATTAGTC
ATCGCTATTACCATGGTGATGCGGTTTTGGCAGTACATCAATGGGCGTGGATAGCGG
TTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACG
CAAATGGGCGGTAGGCGTGTACGGTGGGAGGTCTATATAAGCAGCGCGTTTTGCCT
GTACTGGGTCTCTCTGGTTAGACCAGATCTGAGCCTGGGAGCTCTCTGGCTAACTAG
GGAACCCACTGCTTAAGCCTCAATAAAGCTTGCCTTGAGTGCTTCAAGTAGTGTGTG
CCCGTCTGTTGTGTGACTCTGGTAACTAGAGATCCCTCAGACCCTTTTAGTCAGTGTG
GAAAATCTCTAGCAGTGGCGCCCGAACAGGGACTTGAAAGCGAAAGGGAAACCAG
AGGAGCTCTCTCGACGCAGGACTCGGCTTGCTGAAGCGCGCACGGCAAGAGGCGAG
GGGCGGCGACTGGTGAGTACGCCAAAAATTTTGACTAGCGGAGGCTAGAAGGAGAG
AGATGGGTGCGAGAGCGTCAGTATTAAGCGGGGGAGAATTAGATCGCGATGGGAAA
AAATTCGGTTAAGGCCAGGGGGAAAGAAAAAATATAAATTAAAACATATAGTATGG
GCAAGCAGGGAGCTAGAACGATTCGCAGTTAATCCTGGCCTGTTAGAAACATCAGA
AGGCTGTAGACAAATACTGGGACAGCTACAACCATCCCTTCAGACAGGATCAGAAG
AACTTAGATCATTATATAATACAGTAGCAACCCTCTATTGTGTGCATCAAAGGATAG
AGATAAAAGACACCAAGGAAGCTTTAGACAAGATAGAGGAAGAGCAAAACAAAAG
TAAGACCACCGCACAGCAAGCGGCCGGCCGCTGATCTTCAGACCTGGAGGAGGAGA
TATGAGGGACAATTGGAGAAGTGAATTATATAAATATAAAGTAGTAAAAATTGAAC
CATTAGGAGTAGCACCCACCAAGGCAAAGAGAAGAGTGGTGCAGAGAGAAAAAAG
AGCAGTGGGAATAGGAGCTTTGTTCCTTGGGTTCTTGGGAGCAGCAGGAAGCACTAT
GGGCGCAGCGTCAATGACGCTGACGGTACAGGCCAGACAATTATTGTCTGGTATAG
TGCAGCAGCAGAACAATTTGCTGAGGGCTATTGAGGCGCAACAGCATCTGTTGCAA
CTCACAGTCTGGGGCATCAAGCAGCTCCAGGCAAGAATCCTGGCTGTGGAAAGATA
CCTAAAGGATCAACAGCTCCTGGGGATTTGGGGTTGCTCTGGAAAACTCATTTGCAC
CACTGCTGTGCCTTGGAATGCTAGTTGGAGTAATAAATCTCTGGAACAGATTTGGAA
```

-continued

```
TCACACGACCTGGATGGAGTGGGACAGAGAAATTAACAATTACACAAGCTTAATAC

ACTCCTTAATTGAAGAATCGCAAAACCAGCAAGAAAAGAATGAACAAGAATTATTG

GAATTAGATAAATGGGCAAGTTTGTGGAATTGGTTTAACATAACAAATTGGCTGTGG

TATATAAAATTATTCATAATGATAGTAGGAGGCTTGGTAGGTTTAAGAATAGTTTTT

GCTGTACTTTCTATAGTGAATAGAGTTAGGCAGGGATATTCACCATTATCGTTTCAG

ACCCACCTCCCAACCCCGAGGGGACCCGACAGGCCCGAAGGAATAGAAGAAGAAG

GTGGAGAGAGAGACAGAGACAGATCCATTCGATTAGTGAACGGATCGGCACTGCGT

GCGCCAATTCTGCAGACAAATGGCAGTATTCATCCACAATTTTAAAAGAAAAGGGG

GGATTGGGGGGTACAGTGCAGGGGAAAGAATAGTAGACATAATAGCAACAGACAT

ACAAACTAAAGAATTACAAAAACAAATTACAAAAATTCAAAATTTTCGGGTTTATTA

CAGGGACAGCAGAGATCCAGTTTGGTTAGTACCGGGCCCGCTCTAGAGATCCGACG

CGCCATCTCTAGGCCCGCGCCGGCCCCCTCGCACAGACTTGTGGGAGAAGCTCGGCT

ACTCCCCTGCCCCGGTTAATTTGCATATAATATTTCCTAGTAACTATAGAGGCTTAAT

GTGCGATAAAAGACAGATAATCTGTTCTTTTTAATACTAGCTACATTTTACATGATA

GGCTTGGATTTCTATAAGAGATACAAATACTAAATTATTATTTTAAAAAACAGCACA

AAAGGAAACTCACCCTAACTGTAAAGTAATTGTGTGTTTTGAGACTATAAATATCCC

TTGGAGAAAAGCCTTGTTAACGCGCGGTGACCCTCGAGGTCGACGGTATCGATAAG

CTCGCTTCACGAGATTCCAGCAGGTCGAGGGACCTAATAACTTCGTATAGCATACAT

TATACGAAGTTATATTAAGGGTTCCAAGCTTAAGCGGCCGCGTGGATAACCGTATTA

CCGCCATGCATTAGTTATTAATAGTAATCAATTACGGGTCATTAGTTCATAGCCCA

TATATGGAGTTCCGCGTTACATAACTTACGGTAAATGGCCCGCCTGGCTGACCGCCC

AACGACCCCCGCCCATTGACGTCAATAATGACGTATGTTCCCATAGTAACGCCAATA

GGGACTTTCCATTGACGTCAATGGGTGGAGTATTTACGGTAAACTGCCCACTTGGCA

GTACATCAAGTGTATCATATGCCAAGTACGCCCCCTATTGACGTCAATGACGGTAAA

TGGCCCGCCTGGCATTATGCCCAGTACATGACCTTATGGGACTTTCCTACTTGGCAG

TACATCTACGTATTAGTCATCGCTATTACCATGGTGATGCGGTTTTGGCAGTACATCA

ATGGGCGTGGATAGCGGTTTGACTCACGGGGATTTCCAAGTCTCCACCCCATTGACG

TCAATGGGAGTTTGTTTTGGCACCAAAATCAACGGGACTTTCCAAAATGTCGTAACA

ACTCCGCCCCATTGACGCAAATGGGCGGTAGGCGTGTACGGTGGAGGTCTATATA

AGCAGAGCTGGTTTAGTGAACCGTCAGATCCGCTAGCGCTACCGGTCGCCACCATG

GTGAGCAAGGGCGAGGAGCTGTTCACCGGGGTGGTGCCCATCCTGGTCGAGCTGGA

CGGCGACGTAAACGGCCACAAGTTCAGCGTGTCCGGCGAGGGCGAGGGCGATGCCA

CCTACGGCAAGCTGACCCTGAAGTTCATCTGCACCACCGGCAAGCTGCCCGTGCCCT

GGCCCACCCTCGTGACCACCCTGACCTACGGCGTGCAGTGCTTCAGCCGCTACCCCG

ACCACATGAAGCAGCACGACTTCTTCAAGTCCGCCATGCCCGAAGGCTACGTCCAG

GAGCGCACCATCTTCTTCAAGGACGACGGCAACTACAAGACCCGCGCCGAGGTGAA

GTTCGAGGGCGACACCCTGGTGAACCGCATCGAGCTGAAGGGCATCGACTTCAAGG

AGGACGGCAACATCCTGGGGCACAAGCTGGAGTACAACTACAACAGCCACAACGTC

TATATCATGGCCGACAAGCAGAAGAACGGCATCAAGGTGAACTTCAAGATCCGCCA

CAACATCGAGGACGGCAGCGTGCAGCTCGCCGACCACTACCAGCAGAACACCCCCA
```

-continued

```
TCGGCGACGGCCCCGTGCTGCTGCCCGACAACCACTACCTGAGCACCCAGTCCGCCC
TGAGCAAAGACCCCAACGAGAAGCGCGATCACATGGTCCTGCTGGAGTTCGTGACC
GCCGCCGGGATCACTCTCGGCATGGACGAGCTGTACAAGTAGGAATTCGTCGAGGG
ACCTAATAACTTCGTATAGCATACATTATACGAAGTTATACATGTTTAAGGGTTCCG
GTTCCACTAGGTACAATTCGATATCAAGCTTATCGATAATCAACCTCTGGATTACAA
AATTTGTGAAAGATTGACTGGTATTCTTAACTATGTTGCTCCTTTTACGCTATGTGGA
TACGCTGCTTTAATGCCTTTGTATCATGCTATTGCTTCCCGTATGGCTTTCATTTTCTCCTCC
TTGTATAAATCCTGGTTGCTGTCTCTTTATGAGGAGTTGTGGCCCGTTGTCAGG
CAACGTGGCGTGGTGTGCACTGTGTTTGCTGACGCAACCCCCACTGGTTGGGGCATT
GCCACCACCTGTCAGCTCCTTTCCGGGACTTTCGCTTTCCCCCTCCCTATTGCCACGG
CGGAACTCATCGCCGCCTGCCTTGCCCGCTGCTGGACAGGGGCTCGGCTGTTGGGCA
CTGACAATTCCGTGGTGTTGTCGGGGAAATCATCGTCCTTTCCTTGGCTGCTCGCCTG
TGTTGCCACCTGGATTCTGCGCGGGACGTCCTTCTGCTACGTCCCTTCGGCCCTCAAT
CCAGCGGACCTTCCTTCCCGCGGCCTGCTGCCGGCTCTGCGGCCTCTTCCGCGTCTTC
GCCTTCGCCCTCAGACGAGTCGGATCTCCCTTTGGGCCGCCTCCCCGCATCGATACC
GTCGACCTCGATCGAGACCTAGAAAAACATGGAGCAATCACAAGTAGCAATACAGC
AGCTACCAATGCTGATTGTGCCTGGCTAGAAGCACAAGAGGAGGAGGAGGTGGGTT
TTCCAGTCACACCTCAGGTACCTTTAAGACCAATGACTTACAAGGCAGCTGTAGATC
TTAGCCACTTTTTAAAAGAAAAGGGGGGACTGGAAGGGCTAATTCACTCCCAACGA
AGACAAGATATCCTTGATCTGTGGATCTACCACACACAAGGCTACTTCCCTGATTGG
CAGAACTACACACCAGGGCCAGGGATCAGATATCCACTGACCTTTGGATGGTGCTA
CAAGCTAGTACCAGTTGAGCAAGAGAAGGTAGAAGAAGCCAATGAAGGAGAGAAC
ACCCGCTTGTTACACCCTGTGAGCCTGCATGGGATGGATGACCCGGAGAGAGAAGT
ATTAGAGTGGAGGTTTGACAGCCGCCTAGCATTTCATCACATGGCCCGAGAGCTGCA
TCCGGACTGTACTGGGTCTCTCTGGTTAGACCAGATCTGAGCCTGGGAGCTCTCTGG
CTAACTAGGGAACCCACTGCTTAAGCCTCAATAAAGCTTGCCTTGAGTGCTTCAAGT
AGTGTGTGCCCGTCTGTTGTGTGACTCTGGTAACTAGAGATCCCTCAGACCCTTTTAG
TCAGTGTGGAAAATCTCTAGCAGTTAACGAATTCGGCGCGCcAATtgATCaGCGctTAAgCTA
gcGATCgcGGGACTTTCCACACCCTAACTGACACACATTCCACAGAATTCCCATC
ACAAAGCTCTGACCTCAATCCTATAGAAAGGAGGAATGAGCCAAAATTCACCCAAC
TTATTGTGGGAAGCTGGCCTTGGAGGCCTGTGTGTCAGTTAGGGTGTGGAAAGTCCC
CAGGCTCCCCAGGCAGGCAGAAGTATGCAAAGCATGCATCTCAATTAGTCAGCAAC
CAGGTGTGGAAAGTCCCCAGGCTCCCCAGCAGGCAGAAGTATGCAAAGCATGCATC
TCAATTAGTCAGCAACCATAGTCCCGCCCCTAACTCCGCCCATCCCGCCCCTAACTC
CGCCCAGTTCCGCCCATTCTCCGCCCCATGGCTGACTAATTTTTTTTATTTATGCAGA
GGCCGAGGCCGCCTCTGCCTCTGAGCTATTCCAGAAGTAGTGAGGAGGCTTTTTTGG
AGGCCTAGGCTTTTGCAAAAAGCTCCCGGGAGCTTGTATATCCATTTTCGGATCTGA
TCAGCACGTGTTGACAATTAATCATCGGCATAGTATATCGGCATAGTATAATACGAC
AAGGTGAGGAACTAAACCATGGCCAAGTTGACCAGTGCCGTTCCGGTGCTCACCGC
GCGCGACGTCGCCGGAGCGGTCGAGTTCTGGACCGACCGGCTCGGGTTCTCCCGGG
ACTTCGTGGAGGACGACTTCGCCGGTGTGGTCCGGGACGACGTGACCCTGTTCATCA
```

-continued

```
GCGCGGTCCAGGACCAGGTGGTGCCGGACAACACCCTGGCCTGGGTGTGGGTGCGC

GGCCTGGACGAGCTGTACGCCGAGTGGTCGGAGGTCGTGTCCACGAACTTCCGGGA

CGCCTCCGGGCCGGCCATGACCGAGATCGGCGAGCAGCCGTGGGGCGGGAGTTCG

CCCTGCGCGACCCGGCCGGCAACTGCGTGCACTTCGTGGCCGAGGAGCAGGACTGA

CACGTGCTACGAGATTTCGATTCCACCGCCGCCTTCTATGAAAGGTTGGGCTTCGGA

ATCGTTTTCCGGGACGCCGGCTGGATGATCCTCCAGCGCGGGGATCTCATGCTGGAG

TTCTTCGCCCACCCCAACTTGTTTATTGCAGCTTATAATGGTTACAAATAAAGCAATA

GCATCACAAATTTCACAAATAAAGCATTTTTTTCACTGCATTCTAGTTGTGGTTTGTC

CAAACTCATCAATGTATCTTAAGGCCTTTTCCCCGTATCCCCCCAGGTGTCTGCAGG

CTCAAAGAGCAGCGAGAAGCGTTCAGAGGAAAGCGATCCCGTGCCACCTTCCCCGT

GCCCGGGCTGTCCCCGCACGCTGCCGGCTCGGGGATGCGGGGGGAGCGCCGGACCG

GAGCGGAGCCCCGGCGGCTCGCTGCTGCCCCCTAGCGGGGGAGGGACGTAATTAC

ATCCCTGGGGGCTTTGGGGGGGGCTGTCCCTCTAGAACTAGTGGATCCCCCGGGCT

GCAGGAATTCGATAAAAGTTTTGTTACTTTATAGAAGAAATTTTGAGTTTTTGTTTTT

TTTTAATAAATAAATAAACATAAATAAATTGTTTGTTGAATTTATTATTAGTATGTAA

GTGTAAATATAATAAAACTTAATATCTATTCAAATTAATAAATAAACCTCGATATAC

AGACCGATAAAACACATGCGTCAATTTTACGCATGATTATCTTTAACGTACGTCACA

ATATGATTATCTTTCTAGGGTTAATCTAGCTGCGTGTTCTGCAGCGTGTCGAGCATCT

TCATCTGCTCCATCACGCTGTAAAACACATTTGCACCGCGAGTCTGCCCGTCCTCCA

CGGGTTCAAAAACGTGAATGAACGAGGCGCGCTCACTGGCCGTCGTTTTACAACGTC

GTGACTGGGAAAACCCTGGCGTTACCCAACTTAATCGCCTTGCAGCACATCCCCCTT

TCGCCAGCTGGCGTAATAGCGAAGAGGCCCGCACCGATCGCCCTTCCCAACAGTTG

CGCAGCCTGAATGGCGAATGGGACGCGCCCTGTAGCGGCGCATTAAGCGCGGCGGG

TGTGGTGGTTACGCGCAGCGTGACCGCTACACTTGCCAGCGCCCTAGCGCCCGCTCC

TTTCGCTTTCTTCCCTTCCTTTCTCGCCACGTTCGCCGGCTTTCCCCGTCAAGCTCTAA

ATCGGGGGCTCCCTTTAGGGTTCCGATTTAGTGCTTTACGGCACCTCGACCCCAAAA

AACTTGATTAGGGTGATGGTTCACGTAGTGGGCCATCGCCCTGATAGACGGTTTTTC

GCCCTTTGACGTTGGAGTCCACGTTCTTTAATAGTGGACTCTTGTTCCAAACTGGAAC

AACACTCAACCCTATCTCGGTCTATTCTTTTGATTTATAAGGGATTTTGCCGATTTCG

GCCTATTGGTTAAAAAATGAGCTGATTTAACAAAAATTTAACGCGAATTTTAACAAA

ATATTAACGCTTACAATTTAGGTGGCACTTTTCGGGGAAATGTGCGCGGAACCCCTA

TTTGTTTATTTTTCTAAATACATTCAAATATGTATCCGCTCATGAGACAATAACCCTG

ATAAATGCTTCAATAATATTGAAAAAGGAAGAGT
```

Single cell clones of HEK293T cells were isolated and suspension adapted for transfection of the packaging and transfer vector plasmids. To test and confirm the effect of PIGGYBAC® transposase, the transfection was performed in the absence or presence of PIGGYBAC® transposase mRNA. PEIpro transfection agent was used in the transfection.

To make a packaging cell line for lenti-eGFP, packaging plasmid and transfer vectors encoding eGFP were co-transfected. To make a packing cell line for packaging alone (i.e., no gene of interest expression), the packaging plasmid alone was transfected. Four days post-transfection, the stably transfected cells were selected by adding puromycin and Zeocin for the lenti-eGFP, and puromycin alone for the packaging cell line.

Results

Co-transfection of transposase mRNA significantly enhanced the antibiotic-resistant colonies, indicating that transposase expression indeed promoted the chromosomal integration of the expression cassettes. FIGS. 3A-3D show the results of HEK293T cells transfected with packaging and eGFP transfer vector in the absence (FIGS. 3A and 3C) or presence (FIGS. 3B and 3D) of transposase mRNA (TP mRNA). After 4 days post transfection, antibiotics-resistant cells were selected by adding puromycin (0.5 ug/mL) and Zeocin (300 ug/mL). At 26 days post-transfection, the cells were observed under the fluorescent microscope and images for GFP and black and white (B/W) were collected.

Similarly, co-transfection of transposase mRNA enhanced the antibiotic-resistant colonies during the process of packaging cell line generation (data now shown).

The antibiotic-resistant packaging cell line was amplified and frozen before characterization. The packaging cell encoding LV-eGFP was thawed and cultured in suspension in the presence of puromycin and Zeocin. To induce lentiviral vector production, sodium butyrate (6 mM) and doxycycline (2 ug/mL) were added to the packaging cell culture and further incubated.

Figure 4:
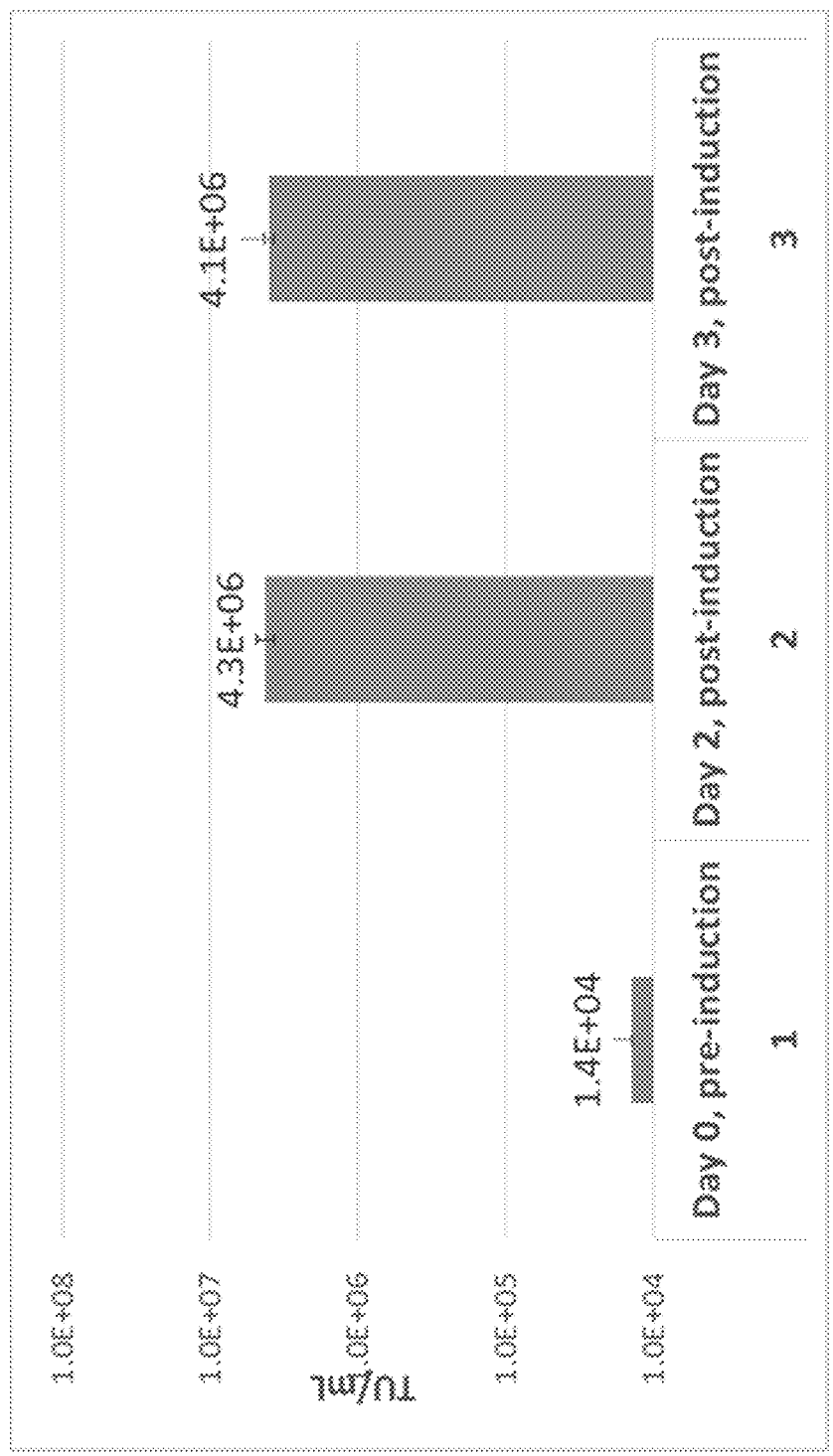
FIG. 4 shows the production of lentiviral vectors using exemplary cell lines described herein.

At day 2 and 3 post-induction, the culture supernatant was collected for the measurement of lentiviral titers. For the measurement of uninduced lentiviral vector titer, the culture supernatant of uninduced sample was used. It was observed that more than 4E6 transduction units/mL of lentiviral vector were produced upon induction (day 2 and day 3) while the basal amount of lentiviral vector production before any induction (day 0) was basal level (FIG. 4).

Example 2: Further Characterization of Lentiviral Producer Cell Line

Figure 5:
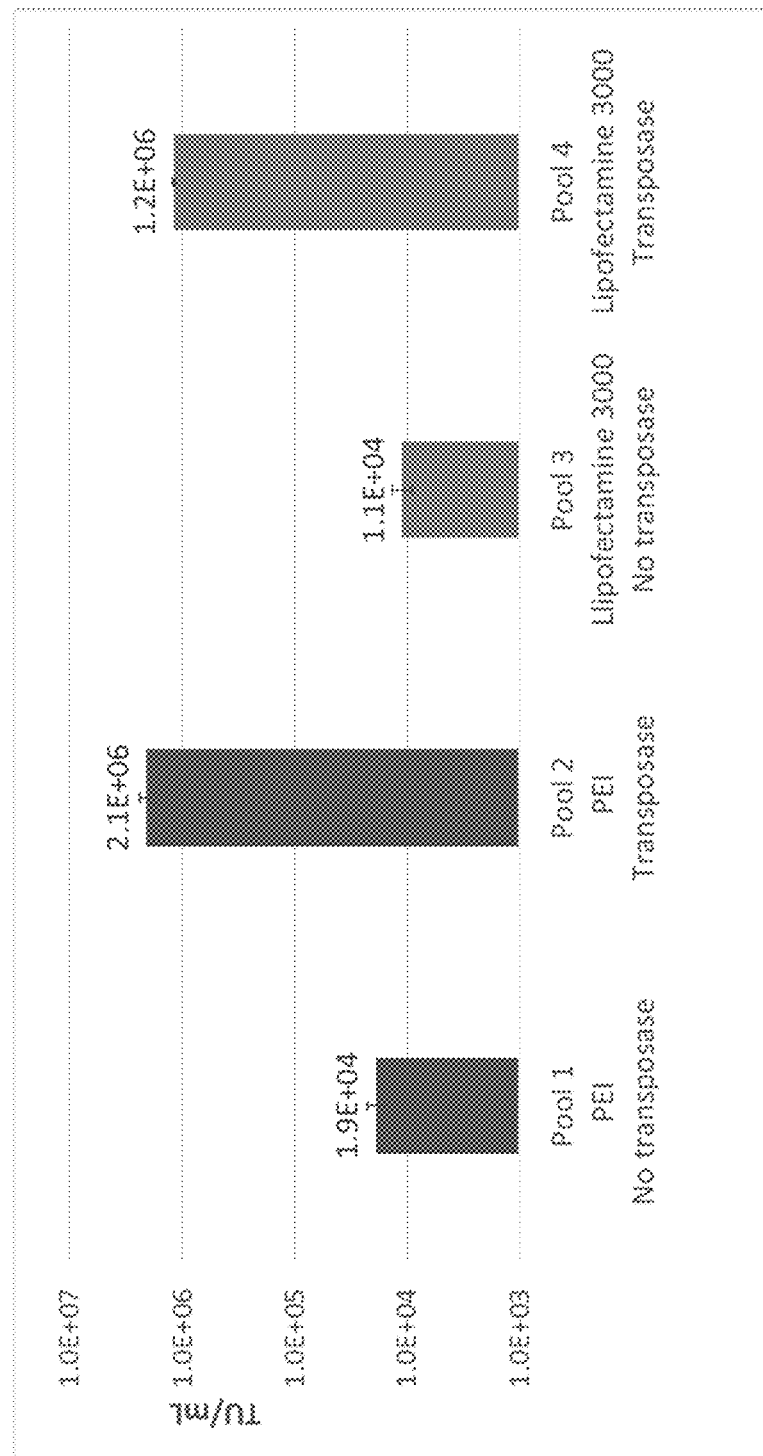
FIG. 5 shows lentivirus titer for PEI and lipofectamine transfection with and without transposase.

A. Additional studies were designed to examine the use of different transfection agents with the vectors described herein. As shown in FIG. 5 both PEI and lipofectamine 3000 successfully increased infectious lentivirus titers from the PCL pools by about 100 times in the presence of PIGGYBAC® transposase mRNA, demonstrating that the expression of the transposase leads to efficient integrations of cargo sequences into the chromosomes of the host cells.

B. Further experiments were conducted to determine the effects of removal of antibiotics on the success of lentiviral production. In such experiments, an HEK-293T, single cell clone (SCC) designated DH4 was selected for demonstrating consistent infectious titers upon induction up to passage 21.

Figure 6:
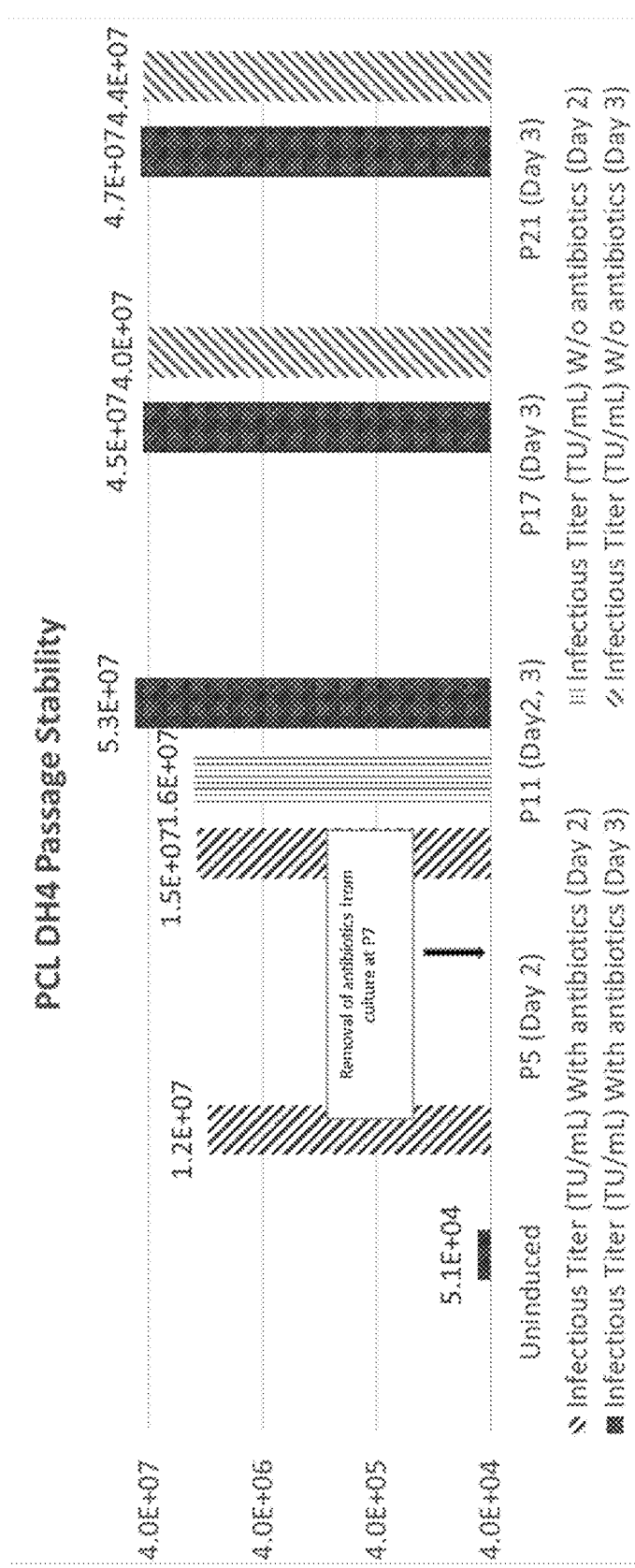
FIG. 6 shows lentivirus productivity and stability of a single cell clone DH4.

As demonstrated in FIG. 6, uninduced cells exhibited a low level of infectious titer. After passage 7 (day 2), the induced cells demonstrated 1.2E7 TU/mL (transduction units/mL). For a selection of the cells, antibiotics were removed, and the cells continued to be passed. At passage 11 (day 2, 3), cells with antibiotics achieved a titer of 1.5E7 TU/mL (day 2) and 5.3E7 TU/mL (day 3). In comparison without antibiotics, the infectious titer still reached 1.6E7 TU/mL on day 2. Extending out to passage 17 and passage 21 (about a seven week period), the viral titer continued to remain at the same level without antibiotics as in the presence of antibiotics (4.4E7). Day 2 vs. Day 3 refers to the days of incubation of the PCLs after induction and before harvest, comparing the effect of an additional day between induction and harvest.

Figure 7:
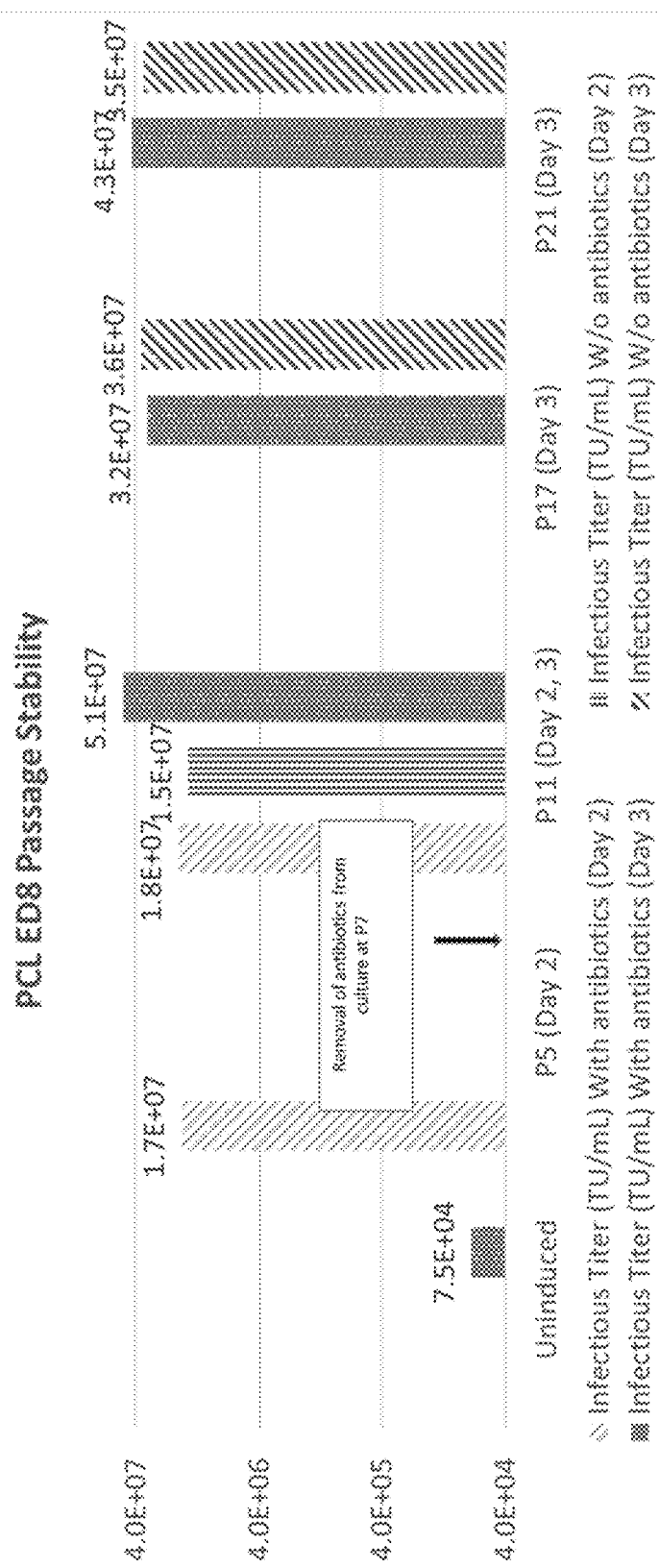
FIG. 7 shows lentivirus productivity and stability of a single cell clone ED8.

FIG. 7 shows similar results using another single cell clone, ED8. As with the DH4 clone, removal of antibiotics at passage 7 did not significantly impact the ability of the cell clone to produce an infectious viral titer of the same scale as cell treated with antibiotic. As noted, by passage 21, an infectious titer of 3.5E7 TU/mL was achieved, similar to the 4.3E7 TU/mL for the cells that were continued to be treated with antibiotics.

Figure 8:
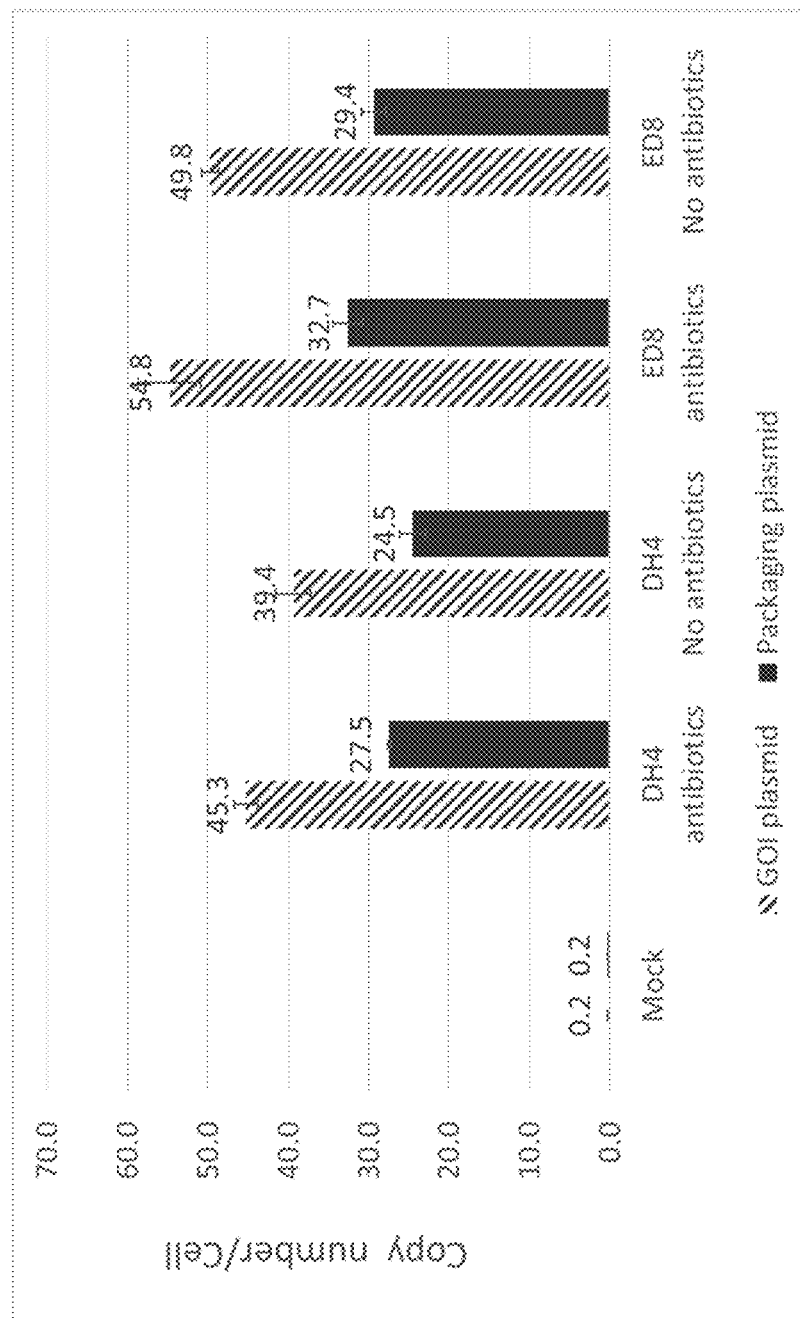
FIG. 8 shows the results of a copy number analysis.

FIG. 8 shows copy numbers (gene of interest or packaging plasmid) integrated into the host cell chromosomes measured using ddPCR assay. The vector copy number (VCN) was calculated by the formula, VCN=copy number of target sequence/copy number of RPP30 (Ribonuclease P/MRP Subunit P30)*2. The primers/probe sets specific to long terminal repeat (LTR) and vesicular stomatitis virus glycoprotein G (VSV-G) were used to detect the GOI and packaging plasmids, respectively. As noted for both cell clones, both the gene of interest and the packaging plasmid were efficiently integrated into the chromosomes of the cells. While the removal of antibiotics during the passage of the cells (again at passage 70) slightly reduced the copy number, there was still sufficient integration of the GOI and packaging plasmid into the cells.

This is a surprising and unexpected result, demonstrating that even in the absence of antibiotics, the producer cell lines prepared according to the methods described herein are able to produce high viral titer. This provides a significant advantage to the manufacturing of lentivirus, as it is highly desirable to remove antibiotics from a producer cell line culture to minimize risks associated with antibiotic contamination, etc., of a product that is to be later utilized in a human patient population.

C. Experiments were also conducted to determine the transduction efficiency of lentiviral vectors produced using the producer cell lines described herein, in comparison with lentivirus produced from transient transfection. Lentivirus was produced using PCL from both the DH4 and ED8 cell lines, along with transient transfection of an HEK-293 cell. Following production, lentiviral vectors were transduced into human peripheral blood mononuclear cells (PBMC) with a multiplicity of infection (MOI) of 5. Briefly, PMBCs were plated at 4E5 cells/well in a 24 well plate. On day 1, the cells were stimulated with IL-2 (15 ng/ml) and anti-CD3 and anti-CD-28 (25 μL/1E6 cells). The cells were then transduced with lentivirus at a multiplicity of infection of 5, using a green fluorescent protein as the gene of interest (GOI). After 5 days, the cells were analyzed using flow cytometry to determine the fraction of fluorescence-positive cells, and transduction efficiency was calculated.

Figure 9:
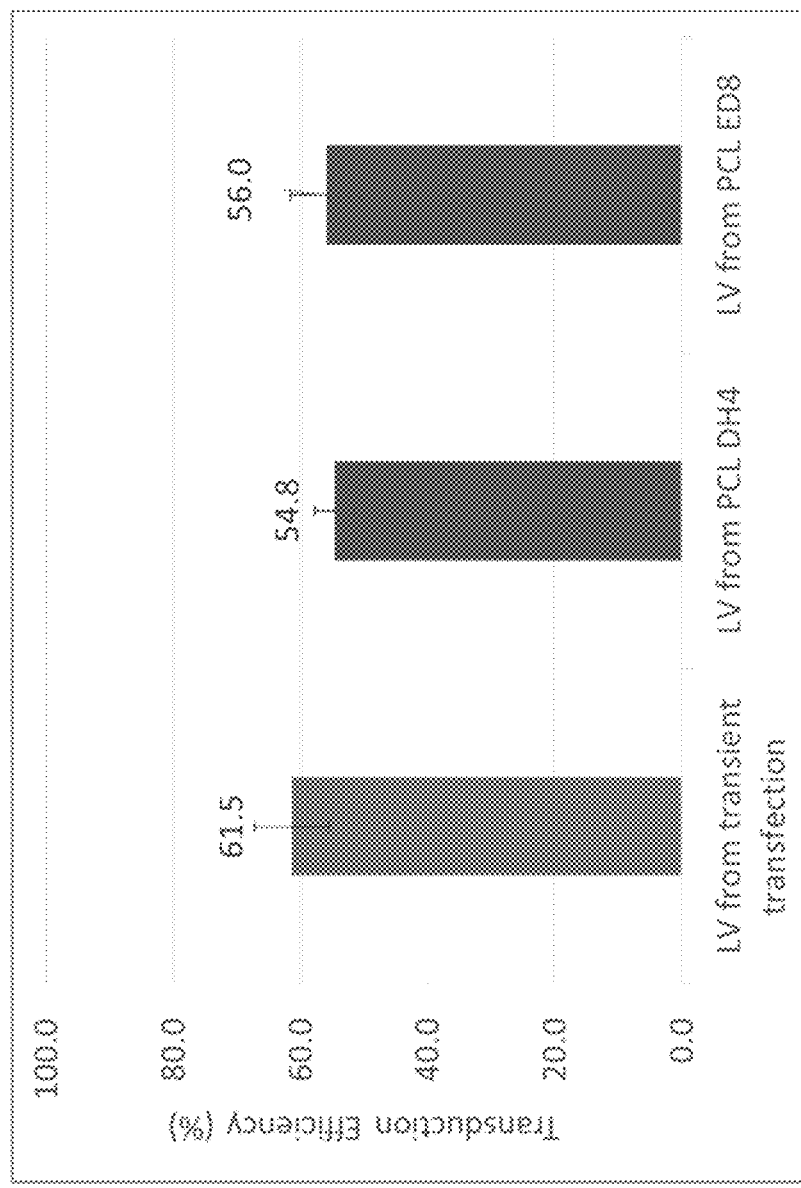
FIG. 9 shows potency comparison for lentivirus produced using transient transfection and producer cell lines.

As demonstrated in FIG. 9, when PMBCs are transduced with a multiplicity of infection of 5, similar transduction efficiency is observed for lentivirus produced using transient transfection methods, when compared with lentivirus produced using PCL (DH4 and ED8 lines) and the methods described herein (between about 55%-62% transduction efficiency).

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

What is claimed is:

1. A method of producing a lentiviral packaging vector-containing mammalian cell, comprising:
   a. transfecting a mammalian cell with:
      i. a packaging vector including an expression cassette, encoding:
         1. a lentiviral regulator of expression of virion proteins (REV) gene under control of a first promoter;
         2. a lentiviral envelope gene under control of a second promoter; and
         3. a lentiviral group specific antigen (GAG) gene and a lentiviral polymerase (POL) gene both under control of a third promoter,
      wherein the expression cassette is flanked on both the 5' and 3' ends by transposon-specific inverted terminal repeats (ITR); and
   b. culturing the transfected mammalian cell; and
   c. isolating the lentiviral packaging vector-containing mammalian cell.

2. The method of claim 1, wherein the mammalian cell is a mammalian cell culture.

3. The method of claim 2, wherein the mammalian cell culture is a suspension culture.

4. The method of claim 3, wherein the mammalian cell is an HEK293T cell.

5. The method of claim 1, wherein the GAG gene is an HIV GAG gene and the POL gene is an HIV POL gene.

6. The method of claim 1, wherein the lentiviral envelope gene is a Vesicular Stomatitis Virus Glycoprotein (VSV-G) gene.

7. The method of claim 1, wherein the first, second and third promoters are derepressible promoters.

8. The method of claim 7, wherein the expression cassette further encodes a repressor element of the first, second and third derepressible promoters.

9. The method of claim 8, wherein each of the derepressible promoters comprises a functional promoter and a tetracycline operator sequence (TetO), and the repressor element is a tetracycline repressor protein.

10. The method of claim 9, wherein the expression cassette further comprises a Kruppel-associated box sequence following a sequence encoding the tetracycline repressor protein.

11. The method of claim 1, wherein the transposon-specific ITRs are Lepidopteran transposon ITRs.

12. The method of claim 1, wherein the transfecting is in the presence of a transposase that recognizes the transposon-specific ITRs.

13. The method of claim 12, wherein the transposase is Lepidopteran transposase mRNA or Lepidopteran transpose cDNA.

* * * * *